United States Patent [19]

Barbachyn et al.

[11] Patent Number: 5,654,428
[45] Date of Patent: Aug. 5, 1997

[54] SUBSTITUTED HETEROARYLPHENYLOXAZOLIDINONES

[75] Inventors: Michael R. Barbachyn, Kalamazoo; Steven J. Brickner, Portage, both of Mich.

[73] Assignee: Pharmacia & Upjohn Company, Kalamazoo, Mich.

[21] Appl. No.: 466,956

[22] Filed: Jun. 6, 1995

Related U.S. Application Data

[60] Division of Ser. No. 233,903, filed as PCT/US92/08267, Oct. 5, 1992, Pat. No. 5,565,571, which is a continuation-in-part of Ser. No. 831,213, Feb. 7, 1992, abandoned, which is a continuation-in-part of Ser. No. 786,107, Nov. 1, 1991, abandoned.

[51] Int. Cl.$^6$ ............ C07D 403/10; C07D 401/10; C07D 403/14; C07D 413/10
[52] U.S. Cl. ............ 544/235; 544/237; 544/238; 544/335; 544/336; 544/353; 544/283; 544/116; 544/139; 544/127; 544/122; 544/120; 540/603; 540/601; 540/600; 540/599; 540/598; 540/597; 546/122; 546/113; 548/232
[58] Field of Search ............ 544/238, 235, 544/237, 335, 336, 353, 283, 122; 548/232; 546/122; 540/603, 599

[56] References Cited

U.S. PATENT DOCUMENTS

| Re. 29,607 | 4/1978 | Oliver et al. | 260/307 |
|---|---|---|---|
| 4,128,654 | 12/1978 | Fugitt et al. | 424/272 |
| 4,250,318 | 2/1981 | Dostert et al. | 548/229 |
| 4,340,606 | 7/1982 | Fugitt et al. | 424/272 |
| 4,461,773 | 7/1984 | Gregory | 424/272 |
| 4,476,136 | 10/1984 | Dostert et al. | 424/272 |
| 4,705,799 | 11/1987 | Gregory | 514/376 |
| 4,801,600 | 1/1989 | Wang et al. | 514/376 |
| 4,921,869 | 5/1990 | Wang et al. | 514/376 |
| 4,948,801 | 8/1990 | Carlson et al. | 514/307 |
| 4,977,173 | 12/1990 | Brittelli et al. | 514/376 |
| 5,164,510 | 11/1992 | Brickner | 548/231 |
| 5,254,577 | 10/1993 | Carlson | 548/229 |

FOREIGN PATENT DOCUMENTS

| 892270 | 8/1982 | Belgium . |
|---|---|---|
| 0127902 | 12/1984 | European Pat. Off. . |
| 0184170 | 11/1985 | European Pat. Off. . |
| 0312000 | 4/1989 | European Pat. Off. . |
| 0316594 | 5/1989 | European Pat. Off. . |
| 0352781 | 1/1990 | European Pat. Off. . |
| 91/07409 | 5/1991 | WIPO . |

OTHER PUBLICATIONS

J. Med. Chem. 33, 2569 (1990).
J. Med. Chem. 32, 1673 (1989).
Tetrahedron 45, 1323 (1989).
Antimicrobial Agents and Chemotherapy 1791 (1987).

*Primary Examiner*—John M. Ford
*Attorney, Agent, or Firm*—Bruce Stein

[57] ABSTRACT

The present invention discloses novel substituted aryl- and heteroarylphenyloxazolidinones which are useful as antibacterial agents. More specifically, the substituted aryl- and heteroarylphenyloxazolidinones of the invention are characterized by oxazolidinones having aryl or heteroaryl group at the p-position of the 3-phenyl ring and additional substitutions at the m-position(s) of the 3-phenyl ring. A compound representative of this new class of oxazolidinones is (±)-5-(acetamidomethyl)-3-[4-(3-pyridyl)-3,5-difluorophenyl]-2-oxazolidinone.

25 Claims, No Drawings

SUBSTITUTED HETEROARYLPHENYLOXAZOLIDINONES

CROSS-REFERENCE TO RELATED APPLICATIONS

The present patent application is a divisional of U.S. Patent application Ser. No. 08/233,903 filed Apr. 28, 1994, now U.S. Pat. No. 5,565,571 which was a continuation application of PCT application PCT/US92/08267, filed Oct. 5, 1992, which was a continuation-in-part application of U.S. Patent application Ser. No. 07/831,213, filed Feb. 7, 1992, (now abandoned) which was a continuation-in-part application of US Patent application Ser. No. 07/786,107, filed Nov. 1, 1991 (now abandoned).

FIELD OF THE INVENTION

The present invention relates to novel substituted aryl- and heteroarylphenyloxazolidinones which are useful as anti-bacterial agents.

BACKGROUND OF THE INVENTION

The oxazolidinones are a class of orally-active, synthetic antibacterial agents. 3-Phenyl-2-oxazolidinones having one or two substitutions on the phenyl ring are known. For one substitution see U.S. Pat. No. 4,948,801, 4,461,773, 4,340, 606, 4,476,136, 4,250,318, 4,128,654, Re 29,607, EP Publication 0 312 000, J. Med. Chem., 32, 1673 (1989), J. Med. Chem., 33, 2569 (1990) and Tetrahedron, 45, 1323 (1989). Compounds of this type include the antibacterial DuP 721, see J. Med. Chem., 32, 1673 (1989).

3-[(di- or fused-ring substituted)phenyl]-2-oxazolidinones are reported in U.S. Pat. Nos. 4,977,173, 4,921,869 and 4,801,600; EP Publications 0 316 594, 0 184 170, and 0 127 902; and U.S. Pat. No. 5,164,510 and WO91/07409.

The present invention is 3-[(di- and tri-substituted) phenyl]-2-oxazolidinones which are effective as antibacterial agents. The compounds of the invention are characterized by oxazolidinones having an aryl or heteroaryl group at the p-position of the 3-phenyl ring and additional substitution(s) at the m-position of the phenyl ring with radicals having an electron-withdrawing effect. These compounds are surprisingly effective as antibacterial agents, since early work by Gregory, et al, in J. Med. Chem., 33, 2569 (1990) suggests compounds having such radicals in the p-position of the phenyl ring are less effective antibacterial agents.

Synthesis of 3-phenyl-2-oxazolidinones and derivatives thereof are well known in the art. However, due to the nature of the radicals, the substituted phenyls of the invention are difficult to synthesize. Thus, we also disclose a process by which the compounds of the invention may be synthesized.

Information Disclosure

The following references disclose 3-phenyl-2-oxazolidinones having a single substitution on the phenyl ring:

U.S. Pat. No. 4,948,801 discloses 3-[(aryl and heteroaryl) phenyl]-2-oxazolidinones having antibacterial activity.

U.S. Pat. No. 4,476,136 discloses 3-[(p-arylalkyl, arylalkenyl, and arylacetylenic substituted)phenyl]-5-(aminomethyl)-2-oxazolidinones which have antibacterial activity.

U.S. Pat. No. 4,461,773 discloses substituted 3-phenyl-5-hydroxymethyl)-2-oxazolidinones which have antibacterial activity.

U.S. Pat. No. 4,340,606 discloses substituted 3-[(p-alkylsulfonyl)phenyl]-5-(hydroxymethyl)- or (acyloxymethyl)-2-oxazolidinones having antibacterial activity in mammals.

U.S. Pat. No. 4,250,318 discloses substituted 3-phenyl-5-(hydroxymethyl)-2-oxazolidinones having antidepressive utility.

U.S. Pat. No. 4,128,654 discloses substituted 3-phenyl-5-(halomethyl)-2-oxazolidinones which are useful in controlling fungal and bacterial diseases of plants.

U.S. Reissue Patent 29,607 discloses substituted 3-phenyl-5-(hydroxymethyl)-2-oxazolidinones having antidepressive, tranquilizing and sedative utility.

Belgian Patent 892,270 discloses the 3-[(arylalkyl, arylalkenyl or arylacetylenic substituted)phenyl]-5-(aminomethyl)-2-oxazolidinones corresponding to U.S. Pat. No. 4,476,136 listed above.

European Patent Publication 0 352 781 discloses aryl and heteroaryl substituted 3-phenyl-2- oxazolidinones corresponding to U.S. Pat. No. 4,948,801 listed above.

European Patent Publication 0 312 000, as reported in Chemical Abstracts 89-116142/16, discloses phenylmethyl and pyridinylmethyl substituted 3-phenyl-2-oxazolidinones.

J. Med. Chem. 33, 2569 (1990) and J. Med. Chem. 32, 1673 (1989); Tetrahedron 45, 1323 (1989); and Antimicrobial Agents and Chemotherapy 1791 (1987) are additional recent references disclosing 3-[(p-substituted) phenyl]-2-oxazolidinones.

The following references disclose 3-[(di-substituted) phenyl]- or 3-[(fused-ring substituted)phenyl]-2-oxazolidinones:

U.S. Pat. No. 4,977,173 discloses 3-phenyl-2-oxazolidinones having a lactam at the p-position and fluorine at the m-position of the phenyl ring (Formula XIII). However, the 3-[(di- or tri-substituted)phenyl]-2-oxazolidinones of the present invention have an aromatic ring at the p-position.

U.S. Pat. Nos. 4,921,869 and 4,801,600 disclose 6'-indolinyl- or alkanoneoxa-zolidinones where the indolinyl nitrogen is meta (m-) to the oxazolidinone nitrogen.

U.S. Pat. Nos. 4,705,799 discloses substituted aminomethyloxooxazolidinyl benzene derivatives including sulfides, sulfoxides, sulfones and sulfonnmides which possess antibacterial activity. However, compounds of the present invention have an aryl or heteroaryl at the p-position of the phenyl ring.

European Patent Publication 0 316 594 discloses substituted 3-(styryl)-2-oxazolidinones corresponding to U.S. Pat. No. 4,977,173 listed above.

European Patent Publications 0 184 170 and 0 127 902 correspond to U.S. Pat. No. 4,705,799, discussed above.

U.S. Pat. No. 5,164,510 and WO91/07409 disclose 3-[(fused-ring substituted)-phenyl]-2- oxazolidinones which are useful as antibacterial agents.

The above references do not disclose the 3-[(di- or tri-substituted)phenyl]-2-oxazolidinones of the present invention.

SUMMARY OF THE INVENTION

Disclosed are substituted aryl- and heteroaryl-phenyl oxazolidinones of Formula (XII)

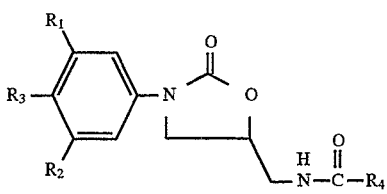

(XII)

where (I) $R_1$ and $R_2$ are the same or different and are selected from the group consisting of
- (a) —H,
- (b) —F,
- (c) —Cl,
- (d) —CF$_3$, and
- (e) —OCH$_3$, provided that only one of $R_1$ or $R_2$ may be hydrogen;

(II) $R_3$ is selected from the group consisting of
- (a) phenyl,
- (b) pyridyl,
- (c) pyrazinyl, (d) pyridazinyl, (e) pyrimidinyl,
- (f) 1,2,3-, (g) 1,2,4-, (h) 1,2,5-triazinyl,
- (i) quinolinyl, (j) isoquinolinyl,
- (k) quinoxalinyl, (l) quinazolinyl, (m) phthalazinyl, (n) cinnolinyl,
- (o) naphthyridinyl,
- (p) indolyl having nitrogen optionally substituted with $R_{5-1}$ where $R_{5-1}$ is
  —H,
  $C_1$-$C_4$ alkyl optionally substituted with one or more halogens,
  $C_3$-$C_6$ cycloalkyl, or
  —C(O)$R_{5-2}$ where $R_{5-2}$ is —H, $C_1$-$C_4$ alkyl optionally substituted with one or more halogens, or
  phenyl optionally substituted with one or more halogens,
- (q) pyrrolopyridinyl having the saturated nitrogen substituted with $R_{5-1}$ where $R_{5-1}$ is as defined above, (r) furanopyridinyl, (s) thienopyridinyl,
- (t) benzothiazolyl, (u) benzoxazolyl,
- (v) imidazolyl having the saturated nitrogen substituted with $R_{5-1}$ where $R_{5-1}$ is as defined above,
- (w) pyrazolyl having the saturated nitrogen substituted with $R_{5-1}$ where $R_{5-1}$ is as defined above,
- (x) thiazolyl, (y) isothiazolyl,
- (z) oxazolyl, (aa) isoxazolyl,
- (bb) pyrroyl having nitrogen substituted with $R_{5-1}$ where $R_{5-1}$ is as defined above,
- (cc) furanyl, (dd) thiophenyl, wherein substitutents (a)-(dd) are optionally substituted with X and Y,
- (ee) 1,2,3-, (ff) 1,2,4-triazolyl having the saturated nitrogen substituted with $R_{5-1}$ where $R_{5-1}$ is as defined above, wherein substituents (ee) and (ff) are optionally substituted with X; (III) each occurrence of Y is independently selected from
- (a) —H,
- (b) —F, (c) —Cl, (d) —Br, (e) —I,
- (f) —$R_{3-1}$, (g) —O$R_{3-1}$, where $R_{3-1}$ is H or $C_1$-$C_4$ alkyl, or
- (h) —NO$_2$;

(IV) each occurrence of X is independently selected from
- (a) —H,
- (b) $C_1$-$C_8$ alkyl optionally substituted with one or more halogens, —OH, =O other than at alpha position, —S(O)$_n R_{3-2}$ where $R_{3-2}$ is $C_1$-$C_4$ alkyl or $C_3$-$C_8$ cycloalkyl, or —N$R_{3-3} R_{3-4}$ where $R_{3-3}$ and $R_{3-4}$ are the same or different and are —H, $C_1$-$C_8$ alkyl, $C_3$-$C_8$ cycloalkyl, —(CH$_2$)$_t$CHO$R_{3-5}$, —(CH$_2$)$_t$N$R_{3-6} R_{3-7}$, or taken together are —(CH$_2$)O(CH$_2$)—, —(CH$_2$)$_t$CH(CO)$R_{3-8}$, or —(CH$_2$)N($R_{3-8}$)(CH$_2$)$_2$—where
  $R_{3-5}$ is —H or $C_1$-$C_4$ alkyl, or
  $R_{3-6}$ and $R_{3-7}$ are the same or different and are —H, $C_1$-$C_4$ alkyl or taken together are —(CH$_2$)$_r$—,
- (c) $C_2$-$C_5$ alkenyl,
- (d) $C_3$-$C_8$ cycloalkyl,
- (e) —O$R_{3-3}$ where $R_{3-3}$ is as defined above,
- (f) —CN,
- (g) —S—(O)$_n$—$R_{3-8}$ where $R_{3-8}$ is $C_1$-$C_4$ alkyl optionally substituted with one or more halogens,
  —OH,
  —CN,
  —N$R_{3-3} R_{3-4}$ where $R_{3-3}$ and $R_{3-4}$ are as defined above, or
  —CO$_2 R_{3-5}$ where $R_{3-5}$ is as defined above, $C_2$-$C_4$ alkenyl,
  —N$R_{3-9} R_{3-10}$ where $R_{3-9}$ is —H, $C_1$-$C_4$ alkyl, or $C_3$-$C_8$ cycloalkyl and $R_{3-10}$ is —H, $C_1$-$C_4$ alkyl, $C_1$-$C_4$ alkenyl, $C_3$-$C_4$ cycloalkyl, —O$R_{3-5}$, or —N$R_{3-6} R_{3-7}$ where $R_{3-5}$, $R_{3-6}$, and $R_{3-7}$ are as defined above,
  —N$_3$, —NHC(O)$R_{3-11}$ where $R_{3-11}$ is $C_1$-$C_4$ alkyl optionally substituted with one or more halogens,
- (h) —S(O)$_2$—N=S(O)$_p R_{3-14} R_{3-15}$ where $R_{3-14}$ and $R_{3-15}$ are the same or different and are $C_1$-$C_2$ alkyl, or taken together are —(CH$_2$)$_q$—,
- (i) —S—C(O)—$R_{3-11}$ where $R_{3-11}$ is as defined above,
- (j) tetrazoly,
- (k) —N$R_{3-3} R_{3-4}$ where $R_{3-3}$ and $R_{3-4}$ are as defined above,
- (l) —N($R_{3-3}$)CO$R_{3-11}$ where $R_{3-3}$ and $R_{3-11}$ are as defined above,
- (m) —N($R_{3-3}$)S(O)$_n R_{3-11}$ where $R_{3-3}$ and $R_{3-11}$ are as defined above,
- (n) —CON$R_{3-3} R_{3-4}$, where $R_{3-3}$ and $R_{3-4}$ are as defined above,
- (o) —C(O)$R_{3-16}$ where $R_{3-16}$ is —H,
  $C_1$-$C_8$ alkyl optionally substituted with one or more halogens,
  $C_1$-$C_4$ alkyl optionally substituted with
  —O$R_{3-5}$,
  —OC(O)$R_{3-5}$,
  —N$R_{3-3} R_{3-4}$,
  —S(O)$_n R_{3-17}$,
  $C_3$-$C_8$ cycloalkyl, or
  $C_2$-$C_5$ alkenyl optionally substituted with —CHO or —CO$_2 R_{3-5}$, where $R_{3-3}$, $R_{3-4}$, and $R_{3-5}$ are as defined above and $R_{3-17}$ is $C_1$-$C_4$ alkyl or $C_3$-$C_8$ cycloalkyl,
- (p) —C(=N$R_{3-18}$)$R_{3-16}$ where $R_{3-16}$ is as defined above and $R_{3-18}$ is —N$R_{3-3} R_{3-4}$, —O$R_{3-3}$, or —NHC(O)$R_{3-3}$ where $R_{3-3}$ and $R_{3-4}$ are as defined above,
- (q) —C$R_{3-16}$(O$R_{3-19}$)O$R_{3-20}$ where $R_{3-16}$ is as defined above and $R_{3-19}$ and $R_{3-20}$ are the same or different and are $C_1$-$C_4$ alkyl, or taken together are —(CH$_2$)$_m$—,

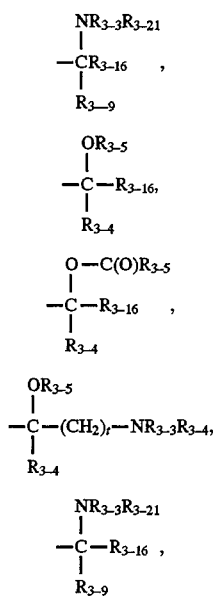

where $R_{3-3}$, $R_{3-4}$, $R_{3-5}$, $R_{3-9}$, and $R_{3-16}$ are as defined above and $R_{3-21}$ is $R_{3-4}$ or $-NR_{3-4}R_{3-5}$ where $R_{3-4}$ and $R_{3-5}$ are as defined above;

m is 2 or 3;
n is 0, 1, or 2;
p is 0 or 1;
q is 3, 4, or 5;
t is 1, 2, or 3;

(V) $R_4$ is selected from the group consisting of
(a) —H,
(b) $C_1$-$C_{12}$ alkyl optionally substituted with 1–3 Cl,
(c) $C_3$-$C_{12}$ cycloalkyl,
(d) $C_5$-$C_{12}$ alkenyl containing one double bond,
(e) phenyl optionally substituted with 1–3 —OH, —OCH$_3$, —OC$_2$H$_5$, —NO$_2$, —F, —Cl, —Br, —COOH and —SO$_3$H, —N(R$_{4-1}$) (R$_{4-2}$) where R$_{4-1}$ and R$_{4-2}$ are the same or different and are —H and C$_1$-C$_5$ alkyl,
(f) furanyl,
(g) tetrahydrofuranyl,
(h) 2-thiophene,
(i) pyrrolidinyl,
(j) pyridinyl,
(k) —O—R$_{4-3}$ where R$_{4-3}$ is C$_1$-C$_4$ alkyl,
(l) —NH$_2$,
(m) —NHR$_{4-4}$ where R$_{4-4}$ is C$_1$-C$_3$ alkyl or —Φ,
(n) —NR$_{4-4}$R$_{4-5}$ where R$_{4-4}$ is as defined above and R$_{4-5}$ is C$_1$-C$_3$ alkyl, or taken together with the attached nitrogen atom to form a saturated mono-nitrogen C$_5$-C$_7$ heterocyclic ring including —O— (morpholine),
(o) —CH$_2$—OH, (p) —CH$_2$—OR$_{4-6}$ where R$_{4-6}$ is C$_1$-C$_4$ alkyl or —CO—R$_{4-7}$ where R$_{4-7}$ is C$_1$-C$_4$ alkyl or —Φ;

and pharmaceutically acceptable salts thereof.

More particularly, the invention discloses compounds of formula (XII) where $R_3$ is a pyridyl or phenyl ting which are optionally substituted with —H, C$_1$-C$_4$ alkyl, or —NR$_{3-3}$R$_{3-4}$.

Most particularly, disclosed are the compounds (±)-5-(acetamidomethyl)-3-[4-(3-pyridyl)-3,5-difluorophenyl]-2-oxazolidinone and (±)-5-(acetamidomethyl)-3-[4-(4-pyridyl)-3,5-difluorophenyl]-2-oxazolidinone.

Another aspect of the invention discloses a process for making a compound of formula (XII) comprising:
(a) converting a substituted aniline to a database derivative,
(b) treating the database derivative to fore an aryl- or heteroaryl-substituted aniline, and
(c) converting the aryl- or heteroaryl-substituted aniline to a aryl- or heteroaryl-substituted phenyloxazolidinone.

More particularly, this aspect of the invention discloses a process for making a compound of formula (XII) wherein step (b) comprises treatment of the stabase derivative with an appropriate alkyl- or aryllithium to form a lithiated derivative, transmetallation with an appropriate electrophilic metal species, addition of an appropriate aryl- or heteroaryl halide or sulfonate precursor in the presence of an appropriate metal catalyst to form a protected aryl- or heteroarylaniline, and removal of the stabase protecting group with aqueous mineral acid.

Most particularly, this aspect of the invention discloses a process for making a compound of formula (XII) wherein step (b) is carried out in a one-pot reaction sequence involving deprotonation of the stabase derivative with n-butyllithium in tetrahydrofuran to form a lithiated derivative, transmetallation with zinc chloride, addition of an aryl- or heteroaryl- bromide, iodide, triflate, or fluorosulfonate in the presence of tetrakis(triphenylphosphine) palladium catalyst to form a protected aryl- or heteroarylaniline, and deprotection with aqueous hydrochloric acid.

Still another aspect of the invention discloses a process for making an oxazolidinone iodide comprising reacting a carbobenzyloxy allyl compound in the presence of an excess of pyridine and iodine, said excess being of equal amounts in the range of 2–20 molar equivalents.

More particularly, this aspect of the invention discloses a process for making an oxazolidinone iodide comprising reacting a carbobenzyloxy allyl compound in the presence of an excess of pyridine and iodine, wherein said excess is in the range of 5–15 molar equivalents.

Most particularly, this aspect of the invention discloses a process for making an oxazolidinone iodide comprising reacting a carbobenzyloxy allyl compound in the presence of an excess of pyridine and iodine, wherein said excess is in the range of 8–10 molar equivalents.

DETAILED DESCRIPTION OF THE INVENTION

It is preferred that $R_1$ or $R_2$ are —F or —CF$_3$; it is most preferred that $R_1$ or $R_2$ are —F.

It is preferred that $R_3$ is phenyl or pyridyl; it is most preferred that $R_3$ is 3-pyridyl or 4-pyridyl.

It is preferred that X is —H, C$_1$-C$_4$ alkyl, or —NR$_{3-3}$R$_{3-4}$; it is most preferred that X is —H.

It is preferred that Y is —H or C$_1$-C$_4$ alkyl; it is most preferred that Y is —H.

It is preferred that $R_4$ is C$_1$-C$_5$ alkyl optionally substituted with 1–3 halogens, C$_3$-C$_5$ cycloalkyl, —NR$_{3-3}$R$_{3-4}$, and —OR$_{3-3}$; it is most preferred that $R_4$ is —CH$_3$.

It is preferred that $R_5$ is C$_1$-C$_4$ alkyl.

The structures of the aryl and heteroaryl groups which comprise R$_3$ (I–XII) are shown in CHART C. Structures (o) (naphthyridinyl), (q) (pyrrolopyridinyl), (r) (furanopyridinyl), and (s) (thienopyridinyl) show the nitrogen-containing heteroaryl abbreviated as Z, where Z is an unsaturated 4-atom linker having one nitrogen and three carbons. In this way, each of the four possible positions for the heteroaryl nitrogen are encompassed by structures (o), (q), (r), and (s).

The aryl- and heteroaryl-substituted phenyloxazolidinones (XII) of the present invention are useful as antibacterial agents in treating infections in mammals caused by gram-positive and anaerobic infections. It is preferred to treat humans and warm-blooded mammals such as cattle, homes, sheep, hogs, dogs, cats, etc., with the aryl- and heteroaryl-substituted phenyl oxazolidinones (XII) of the present invention.

The aryl- and heteroaryl-substituted phenyloxazolidinones (XII) of the present invention are also useful in treating patients infected with one or more Mycobacterium spp. Of particular interest, the aryl- and heteroaryl-substituted phenyloxazolidinones (XII) of the invention are useful in treating patients infected with M. tuberculosis and M. avium.

The aryl- and heteroaryl-substituted phenyloxazolidinones (XII) of the invention can be administered in a manner and in dosage forms similar to those of the known phenyloxyolidinones described above. For example, administration can be either parenteral (IV, IM, SQ) or oral. The daily dose is about 3 to about 30 mg/kg. This dose can preferably be given in divided doses and administered 2–4 times daily. The preferred route of administration as well as the particular dosage form for either the parenteral or oral route depends on the particular facts of the situation including the nature of the infection and condition of the patient. The usual pharmaceutical dosage fores appropriate for parenteral (mixture, suspension in off) and oral (tablet, capsule, syrup, suspension, etc) administration are known to those skilled in the art and there is nothing unusual about using those dosage forms with the aryl- and heteroaryl-substituted phenyloxazolidinones (XII). The exact dosage of the aryl- and heteroaryl-substituted phenyloxazolidinones (XII) to be administered, the frequency of administration, route of administration, and the dosage form will vary depending on a n-tuber of factors known to those skilled in the art including the age, weight, sex, general physical condition of the patient, the nature of the infection (particular microorganism involved, its virulence, the extent of the infection) other medical problems of the patient, etc., as is well known to the physician treating infectious diseases.

The aryl- and heteroaryl-substituted phenyloxazolidinones (XII) can be used either alone or in conjunction with other antibacterial agents as is known to those skilled in the art. Further, the aryl- and heteroaryl-substituted phenyloxazolidinones (XII) can be used in conjunction with non-antibacterial agents as is known to those skilled in the art.

Suitable pharmaceutical salts include the acid addition salts when a basic group is present, such as occurs with the preferred pyridyl group. The acid addition salts including those made from mineral acids, e.g., hydrochloric, hydrobromic, sulfuric, phosphoric, etc., organic sulfonic acids, e.g., methanesulfonic, organic carboxylic acids, e.g., amino, and carbohydrate acids, e.g., gluconic, galacturonic, etc. It is also appreciated by those skilled in the art that the appropriate N-oxides of $R_3$ heteroaryls and tertiary amino substituted aryls are included within the scope of the aryl- and heteroaryl-substituted phenyloxazolidinones (XII) of the invention.

The pharmaceutically active aryl- and heteroaryl-substituted phenyloxazolidinones (XII) of this invention are prepared as described briefly here and in more detail in the examples which follow. CHART A describes the synthesis of the aryl- and heteroaryl-substituted aniline (VI) compounds.

These aniline compounds (VI) are then subsequently reacted following procedures known, or readily acquired by one skilled in the art. These subsequent procedures parallel those described in U.S. Pat. Nos. 4,705,799, WO91/07409, U.S. Pat. No. 5,164,510, and J. Med. Chem., 32, 1673 (1989), all of which are incorporated herein by reference. The Cardillo-Ohno reaction is discussed in Tetrahedron 43, 2505 (1979) and Tetrahedron Lett., 28, 3123 (1987), both of which are also incorporated herein by reference.

CHART A demonstrates a method of preparation of the aryl- and heteroaryl-substituted anilines of the invention. The starting point is a mono- or disubstituted aniline (I). These materials are readily available from a number of commercial vendors. Alternatively, the anilines (I) are known in the chemical literature and may be readily prepared by one skilled in the art. The substituted aniline (I) is treated with n-butyllithium and 1,2-bis(chlorodimethylsilyl)ethane to form the stabase (SB) derivative (II). The SB derivative (II) is converted, in a one-pot reaction sequence, to the crude aryl- and heteroaryl-substituted aniline (VI). This sequence involves slow addition of n-butyllithium to (II), resulting in the aryllithium (III). The aryllithium (III) is transmetallated with anhydrous zinc chloride in tetrahydrofuran (THF) to give an organo zinc derivative (IV). Alternatively, the transmetallation can be carried out with trimethylberate to give the corresponding boric acid, or with tributyltin chloride to give the corresponding stannane. These species react in a manner analogous to that of the organozinc derivative (IV). Addition of the appropriate aryl or heteroaryl iodide, bromide, trifluoromethane sulfonate (triflate), or fluorosulfonate and palladium catalyst, preferably, tetrakis(triphenylphosphine)palladium, followed by warming to reflux temperature gives the coupled product (V). The reaction is quenched with aqueous mineral acid, preferably hydrochloric, to give the aryl- or heteroaryl-substituted aniline (VI). The product (VI) may then be further purified following chromatographic techniques well known in the art. Alternatively, the chromatographic purification may be delayed until after the carbobenzoxy group is appended.

The remaining synthetic steps which lead to the aryl- and heteroaryl-substituted phenyl oxazolidinone (XII) of the invention are outlined in CHART B and closely parallel the procedure found in that discussed in U.S. Pat. No. 4,705,799, WO91/07409, U.S. Pat. No. 5,164,510 and J. Med. Chem., 32, 1673 (1989). Briefly, the aniline (VI) is converted to the carbobenzoxy derivative (VII) in the presence of base and THF. Alkylation of (VII) with allyl halide, preferably bromide, gives the alkylated product (VIII). This intermediate (VIII) is subjected to a modified Cardillo-Ohno iodocyclocarbamation reaction wherein an excess of pyridine in combination with the iodine, is added to facilitate formation of the oxazolidinone iodide (IX). The iodocyclocarbamation reaction as disclosed by Cardillo-Ohno requires 2–3 equivalents of iodine ($I_2$), whereas when synthesizing the compounds of the invention an amount of pyridine and iodine is added which is in the range of 2–20 molar equivalents of each compound. Preferably, 5–15 equivalents should be employed, most preferred is 8–10 equivalents. In addition, we have found that this process has utility in reactions where benzyl iodide is formed and the product so formed competes in the reaction for the substrate and/or product to form unwanted benzylated products. This process, then, is useful to improve yields because it is believed that the excess pyridine traps the benzyliodide to inhibit this competitive reaction. In the synthesis of the compounds of the invention an excessive of pyridine is necessary; when pyridine is omitted from the reaction mixture essentially none of the compounds of the invention are recovered.

After the formation of the iodide (IX) purification may be accomplished following chromatography procedures known in the art. However, this is not necessary as the iodide (IX) may be directly converted to the corresponding azide (X) by treatment with sodium azide in the presence of DMF. Reduction of (X) in the presence of hydrogen, methanol or ethyl acetate, and palladium catalyst affords the amine (XI). Acetylation of the amine (XI) provides the aryl-and heteroaryl-substituted phenyloxazolidinones (XII) of the invention.

The aryl- and heteroaryl-substituted phenyloxazolidinones (XII) of the invention contain at least one chiral center. It is apparent to one skilled in the art that when one chiral center is present, the compound can exist as one of two possible optical isomers [(R) and (S) enantiomers] or a racemic mixture of both. Both individual (R) and (S) enantiomers, as well as mixtures thereof, are within the scope of aryl- and heteroaryl-substituted phenyloxazolidinones (XII) of the invention. In the event a second chiral center is present in the aryl- and heteroaryl-substituted phenyloxazolidinones (XII) of the invention, the resultant diastereomers, in racemic and enantiomerically enriched forms, are also within the scope of the compounds (XII) of the invention.

The enantiomer which is pharmacologically active is the enantiomer with the "S" configuration. The racemic mixture is useful in the same way and for the same purpose as the pure S-enantiomer; the difference is that twice as much racemic material must be used to produce the same effect as the pure S-enantiomer. If desired, the mixture of enantiomers is resolved by means known to those skilled in the art. It is preferable to resolve the racemic mixture at the stage of the compounds (XI) using methods known to those skilled in the art, see for example, Optical Remixture Procedures for Chemical Compounds, Vol 1,: Amines and Related Compounds, Paul Newman, Optical Remixture Information Center, Manhattan College, Riverdale, N.Y., 10471, 1978. For example, treatment of the d,1-amino mixture (XI) with an optically active acid such as (+)-tartaric acid or alternatively with (−)-tartaric acid, would yield a mixture of diastereomeric salts, which can be separated most conveniently by fractional crystallization to give a salt containing only one enantiomer of the racemic mixture. Other suitable optically active acids include, (−) dibenzoyltartaric acid, (+)-camphoric acid, (+)- and (−)-medic acid and (+)-camphor-10-sulfonic acid. By reacting the diastereomeric salt with a base one obtains the enantiomer as the free amino compound (XI). These optically pure compounds are then used in the same way as the racemic mixture.

Charts D and E depict alternative and preferred routes to enantiomerically enriched substituted aryl- and heteroarylphenyloxazolidinones of formula XII which are the subject of this invention. It will be apparent to those skilled in the art that these are merely representative examples, and that slight modifications of the provided synthetic protocols will allow for the preparation of further enantiomerically enriched examples of the oxazolidinones of the invention. The reaction of an isocyanate with racemic and enantiomerically enriched glycidol derivatives to give oxazolidinones is a known and facile process. (See e.g., *Tetrahedron Letter*, 809 (1971); *J. Med. Chem.*, 32, 1673 (1989); *J. Med. Chem.*, 33, 2569 (1990); *J. Med. Chem.*, 35, 1156 (1992); U.S. Pat. No. 4,705,799 (1987)). As shown in Chart D, an isocyanate of structure (1) can be reacted with commercially available (R)-glycidyl butyrate (see, e.g., W. E. Ladner, G. M. Whitesides; *J. Am. Chem. Soc.*, 106:7250 (1984), available from Aldrich Chemical Company, Inc.) in the presence of catalytic lithium bromide and tributyl-phosphine oxide and in a suitable solvent such as xylene and at a suitable temperature (e.g. reflux) to provide the oxazolidinone intermediate (2). The butyryl group is then removed by reaction with an alkoxide, preferably sodium methoxide in methanol, to furnish the key hydroxymethyloxazolidinone intermediate (3). The most preferred route to the alcohol (3) involves the deprotonation of an appropriate CBz-protected aniline of structure (4), readily prepared by standard Schotten-Baumann conditions or other variations known to one skilled in the art, with a suitable base such as n-butyllithium in a suitable solvent such as tetrahydrofuran and at a suitable temperature such as −78° to −60°. Addition of the (R)-glycidyl butyrate, followed by warming to stublent temperature, then directly fords the hydroxymethyloxazolidinone (3), identical in all respects with material prepared via the isocysnate sequence. Compound (3) is then converted to the corresponding methanesulfonate (mesylate) or p-toluenesulfonate (tosylate) derivative (5) or the like, by the action of methanesulfonyl chloride/pyridine or methanesulfonyl chloride/triethylamine/dichloromethane or p-toluenesulfonyl chloride/pyridine. The resultant sulfonate is then reacted with an azide source, for example sodium or potassium azide, in a dipolar aprotic solvent such as N,N-dimethylformamide (DMF) or 1-methyl-2-pyrrolidinone optionally in the presence of a catalyst such as 18-crown-6 at a temperature of 50° to 90° to afford the azide (6). The azide (6) is then reduced by hydrogenation with palladium on carbon or a platinum-based catalyst in an appropriate solvent such as ethyl acetate or methanol (or combinations thereof) to give the aminomethyloxazolidinone (7). Alternatively, the azide may be reduced by treatment with a trivalent phosphorus compound such as triphenylphosphine in the presence of water and in a suitable solvent such as tetrahydrofuran (THF). Compound (7) is then acylated by reactions known to those skilled in the art to give the intermediates of structure (8). Compound (8) is then iodinated with iodine monochloride in acetic acid or acetic acid/trifluoroacetic add (see, e.g., U.S. Pat. No. 4,705,799 (1987)) at a temperature from 0° to 70° or with iodine and silver trifluoroacetate (see e.g., *J. Med. Chem.*, 33, 2569 (1990); and J. Med. Chem., 35, 1156 (1992)) to furnish the enantiomerically enriched substituted iodophenyloxazolicinone intermediate (9). Alternatively, (8) can be brominated with N-bromosuccinimide to give the corresponding bromophenyl- oxazolidinone of structure 9.

Further elaboration of the intermediates of Formula (9) to make the enantiomerically enriched substituted aryl- and heteroarylphenylodolidinones of formula XII which are the subject of this invention is outlined in Chart E. Compound (9) is reacted with the desired aryl- or heteroaryl-substituted metal of formula $R^3M$ (M=trialkyltin, boronic acid or ester, or halozinc) in the presence of a suitable palladium catalyst such as tetrakis(triphenylphosphine)palladium or bis (triphenylphosphine)palladium chloride in a suitable solvent such as DMF or 1,4-dioxane at a suitable temperature (typically 70°–100° C.) to afford the coupled aryl- or heteroarylphenyloxa-zolidinone products of structure XII. Alternatively, the iodo- or bromophenyloxazolidinone of formula (9) is converted to the corresponding trimethyltin derivative (11) by treating it with hexa-methylditin in the presence of a suitable palladium catalyst such as tetrakis (triphenylphosphine)-palladium or bis(triphenylphosphine) palladium chloride in a suitable solvent such as DMF or 1,4-dioxane at a suitable temperature (typically 70° to 100° C.). Intermediate (11) is then treated with the desired aryl or heteroaryl halide of formula $R^3X$ (X=Br or I) in the presence of a suitable palladium catalyst such as tetrakis-(triphenylphosphine)palladium or bis(triphenyl-phosphine) palladium chloride in a suitable solvent such as DMF or 1,4-dioxane at a suitable temperature (typically 70° –100° C.) to afford the enantiomerically enriched aryl- or heteroaryl-phenyloxazolidinone products of structure XII which are the subject of this invention. This latter route (proceeding through 11) is exemplified in the supplemental experimental section by a racemic Example 55.

The definitions and explanations below are for the terms as used throughout this entire document including both the specification and the claims.

Conventions

The chemical formulas representing various compounds or molecular fragments in the specification and claims may contain variable substituents in addition to expressly defined structural features. These variable substituents are identified by a letter or a letter followed by a numerical subscript, for example, "$Z_i1$" or "$R_i$" where "i" is an integer. These variable substituents are either monovalent or bivalent, that is, they represent a group attached to the formula by one or two chemical bonds. For example, a group $Z_1$ would represent a bivalent variable if attached to the formula $CH_3$—$C(=Z_1)H$. Groups $R_i$ and $R_j$ would represent monovalent variable substituents if attached to the formula $CH_3$—$CH_2$—$C(R_iXR_j)H_2$. When chemical formulas are drawn in a linear fashion, such as those above, variable substituents contained in parentheses are bonded to the atom immediately to the left of the variable substituent enclosed in parenthesis. When two or more consecutive variable substituents are enclosed in parentheses, each of the consecutive variable substituents is bonded to the immediately preceding atom to the left which is not enclosed in parentheses. Thus, in the formula above, both $R_i$ and $R_j$ are bonded to the preceding carbon atom.

Chemical formulas or portions thereof drawn in a linear fashion represent atoms in a linear chain. The symbol "—" in general represents a bond between two atoms in the chain. Thus, $CH_3$—O—$CH_2$—$CH(R_i)$—$CH_3$ represents a 2-substituted-1-methoxypropane compound. In a similar fashion, the symbol "=" represents a double bond, e.g., $CH_2$=$C(R_i)$—O—$CH_3$, and the symbol "≡" represents a triple bond, e.g., HC≡C—$CH(R_i)$—$CH_2$—$CH_3$. Carbonyl groups are represented in either one of two ways: —CO— or —C(=O)—, with the former being preferred for simplicity.

Chemical formulas of cyclic (ring) compounds or molecular fragments can be represented in a linear fashion. Thus, the compound 4-chloro-2-methylpyridine can be represented in linear fashion by N*=$C(CH_3)$—CH=CCl—CH=C*H with the convention that the atoms marked with an asterisk (*) are bonded to each other resulting in the formation of a ring. Likewise, the cyclic molecular fragment, 4-(ethyl)-1-piperazinyl can be represented by —N*—$(CH_2)_2$—$N(C_2H_5)$—$CH_2$—C*$H_2$.

A rigid cyclic (ring) structure for any compounds herein defines an orientation with respect to the plane of the ring for substituents attached to each carbon atom of the rigid cyclic compound. For saturated compounds which have two substituents attached to a carbon atom which is part of a cyclic system, —$C(X_1)(X_2)$—the two substituents may be in either an axial or equatorial position relative to the ring and may change between axial/equatorial. However, the position of the two substituents relative to the ring and each other remains fixed. While either substituent at times may lie in the plane of the ring (equatorial) rather than above or below the plane (axial), one substituent is always above the other. In chemical structural formulas depicting such compounds, a substituent ($X_1$) which is "below" another substituent ($X_2$) will be identified as being in the alpha ($\alpha$) configuration and is identified by a broken, dashed or dotted line attachment to the carbon atom, i.e., by the symbol "- - -" or ". . .". The corresponding substituent attached "above" ($X_2$) the other ($X_1$) is identified as being in the beta ($\beta$) configuration and is indicated by an unbroken line attachment to the carbon atom.

When a variable substituent is bivalent, the valences may be taken together or separately or both in the definition of the variable. For example, a variable $R_i$ attached to a carbon atom as —$C(=R_i)$— might be bivalent and be defined as oxo or keto (thus forming a carbonyl group (—CO—)) or as two separately attached monovalent variable substituents $\alpha$-$R_{i-j}$ and $\beta$-$R_{i-k}$. When a bivalent variable, $R_i$, is defined to consist of two monovalent variable substituents, the convention used to define the bivalent variable is of the form "$\alpha$-$R_{i-j}$:$\beta$-$R_{i-k}$" or some variant thereof. In such a case both $\alpha$-$R_{i-j}$ and $\beta$-$R_{i-k}$ are attached to the carbon atom to give —$C(\alpha$-$R_{i-j})(\beta$-13 $R_{i-k})$—. For example, when the bivalent variable $R_6$, —$C(=R_6)$— is defined to consist of two monovalent variable substituents, the two monovalent variable substituents are $\alpha$-$R_{6-1}$:$\beta$-$R_{6-2}$, . . . $\alpha$-$R_{6-9}$:$\beta$-$R_{6-10}$, etc., giving —$C(\alpha$-$R_{6-1})(\beta$-$R_{6-2})$—, . . . —$C(\alpha$-$R_{6-9}(\beta$-$R_{6-10})$—, etc. Likewise, for the bivalent variable $R_{11}$, —$C(=R_{11})$—, two monovalent variable substituents are $\alpha$-$R_{11-1}$:$\beta R_{11-2}$. For a ring substituent for which separate $\alpha$ and $\beta$ orientations do not exist (e.g. due to the presence of a carbon double bond in the ring), and for a substituent bonded to a carbon atom which is not part of a ring the above convention is still used, but the $\alpha$ and $\beta$ designations are omitted.

Just as a bivalent variable may be defined as two separate monovalent variable substituents, two separate monovalent variable substituents may be defined to be taken together to form a bivalent variable. For example, in the formula —$C_1(R_i)H$—$C_2(R_j)H$— ($C_1$ and $C_2$ define arbitrarily a first and second carbon atom, respectively) $R_i$ and $R_j$ may be defined to be taken together to form (1) a second bond between $C_1$ and $C_2$ or (2) a bivalent group such as oxa (—O—) and the formula thereby describes an epoxide. When $R_i$ and $R_j$ are taken together to form a more complex entity, such as the group —X—Y—, then the orientation of the entity is such that $C_1$ in the above formula is bonded to X and $C_2$ is bonded to Y. Thus, by convention the designation ". . . $R_i$ and $R_j$ are taken together to form —$CH_2$—$CH_2$—O—CO— . . . " means a lactone in which the carbonyl is bonded to $C_2$. However, when designated ". . . $R_j$ and $R_i$ are taken together to form —CO—O—$CH_2$—$CH_2$—the convention means a lactone in which the carbonyl is bonded to $C_1$.

The carbon atom content of variable substituents is indicated in one of two ways. The first method uses a prefix to the entire name of the variable such as "$C_1$-$C_4$", where both "1" and "4" are integers representing the minimum and maximum number of carbon atoms in the variable. The prefix is separated from the variable by a space. For example, "$C_1$-$C_4$ alkyl" represents alkyl of 1 through 4 carbon atoms, (including isomeric forms thereof unless an express indication to the contrary is given). Whenever this single prefix is given, the prefix indicates the entire carbon atom content of the variable being defined. Thus $C_2$-$C_4$ alkoxy-carbonyl describes a group $CH_3$—$(CH_2)_n$—O—CO— where n is zero, one or two. By the second method, the carbon atom content of only each portion of the definition is indicated separately by enclosing the "$C_i$—$C_j$" designation in parentheses and placing it immediately (no intervening space) before the portion of the definition being defined. By this optional convention ($C_1$-$C_3$) alkoxycarbonyl has the same meaning as $C_2$-$C_4$ alkoxycarbonyl because the "$C_1$-$C_3$" refers only to the carbon atom content of the alkoxy group. Similarly while both $C_2$-$C_6$ alkoxyalkyl and ($C_1$-$C_3$)alkoxy-($C_1$-$C_3$)alkyl define alkoxyalkyl groups containing from 2 to 6 carbon atoms, the two definitions differ since the former definition allows either the alkoxy or alkyl portion alone to contain 4 or 5 carbon atoms while the latter definition limits either of these groups to 3 carbon atoms.

Definitions

All temperatures are in degrees Centigrade.

TLC refers to thin-layer chromatography.

Brine refers to an aqueous saturated sodinto chloride mixture.

DMF refers to N,N-dimethylformamide.

THF refers to tetrahydrofuran.

CBZ refers to carbobenzyloxy.

n-BuLi refers to n-butyl lithium

SG refers to silica gel.

IR refers to infrared spectroscopy; FTIR refers to Fourier Transform IR.

NMR refers to nuclear (proton) magnetic resonance spectroscopy, chemical shifts are reported in ppm (δ) downfield from tetramethylsilane.

—Φ refers to phenyl ($C_6H_5$).

MS refers to mass spectrometry expressed as m/e or mass/charge

HRMS refers to high remixture mass spectrometry.

$[M +H]^+$ refers to the positive ion of a parent plus a hydrogen atom.

EI refers to electron impact.

CI refers to chemical ionization.

FAB refers to fast atom bombardment.

Ether refers to diethyl ether.

Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

When solvent pairs are used, the ratios of solvents used are volume/volume (v/v). When the solubility of a solid in a solvent is used the ratio of the solid to the solvent is weight/volume (wt/v).

Stabase refers to a particular protecting group for amines (—$NH_2$). The chemical composition is —$Si(CH_3)_2$—$CH_2$—$CH_2$—$Si(CH_3)_2$— and it forms a five member heterocyclic ring, the fifth member is the nitrogen of the amino group.

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

PREPARATION 1 N,N-[1,2-Bis(dimethylsilyl)ethane]-3,5-difluoroaniline

Anhydrous THF (135 ml) is added to 3,5-difluoroaniline (8.64 g, 66.9 mmol) under a nitrogen atmosphere. The resulting mixture is cooled in a dry ice-isopropanol bath and stirred. n-Butyl lithium (1.6M in hexanes, 88 ml, 141 mmol, 2.1 eq) is added to the reaction mixture. The reaction temperature is maintained between –70° and –40° during the addition. After an additional 20 min, 1,2-bis (chlorodimethylsilyl)ethane (14.4 g, 66.9 mmol, 1 eq) in 135 ml of anhydrous THF is slowly added. The homogenous mixture is allowed to stir for an additional 45 min and then warmed to 20°–25°. The reaction is carefully quenched with water (200 ml) and extracted with ether (4×200 ml). The combined organic phases are washed with brine, dried (sodium sulfate), filtered and concentrated under reduced pressure to a solid. The crude material is purified by sublimation (5 torr, 40°) to give the title compound, mp 71°–72°; FTIR (neat) 2958, 2928, 1626, 1581, 1476, 1453, 1345, 1248 and 995 $cm^1$; MS (EI, m/z) 271, 256, 228 and 73; NMR ($CDCl_3$) 6.36, 6.29, 0.85 and 0.25 δ.

PREPARATION 2 4-(3-Pyridyl)-3,5-difluoroaniline

THF (27 ml) is added to N,N-[1,2-bis(dimethylsilyl) ethane]-3,5-difluoroaniline (PREPARATION 1, 1.82 g, 6.72 mmol) under a nitrogen atmosphere. The resulting mixture is cooled to –70°. To the cold mixture is added n-butyl lithium (1.6M in hexanes, 5.03 ml, 8.06 mmol, 1.2 eq) via a syringe pump (0.12 ml/min). After the addition is complete, the reaction mixture is allowed to stir for an additional 20 min and then zinc chloride (1.0 M in THF, 8.06 ml, 8.06 mmol, 1.2 eq) is added. The reaction is warmed to –40° for 15 min. To the reaction mixture is added tetrakis (triphenylphosphine)palladium(0) (773 mg, 0.672 mmol, 0.10 eq) in THF (50 ml) followed by 3-bromopyridine (647 µl, 6.72 mmol, 1.0 eq). The cooling bath is removed and the reaction is warmed to 20°–25°. The reaction is heated to reflux temperature for 16 hr. After this time, the reaction is quenched with aqueous hydrochloric acid (10%, 100 ml). The resulting suspension is vigorously stirred for 0.5 hr and then washed with ether (3×50 ml). The recovered aqueous layer is adjusted to pH 14 with 50% sodium hydroxide (aq) and then extracted with (4×50 ml) ether. The combined organic extracts are washed with brine, dried (sodinto sulfate), filtered and concentrated under reduced pressure to give a solid. This crude material is purified by silica gel chromatography (200 g of silica gel), eluted with acetonitrile/chloroform (5/95 - 1l, 10/90 - 1l, 15/85 - 1l). The appropriate fractions are pooled and concentrated to give the title compound, mp 141°–142°; FTIR (mull) $cm^{-1}$ 3141, 1634, 1460, 1164, 1012, 708; MS (EI, m/z) 206, 205, 179, 158 and 89; NMR ($CDCl_3$) δ 8.67, 8.55, 7.75, 7.35, 6.31 and 4.01.

PREPARATION 3 N-Carbobenzyloxy-4-(3-pyridyl)-3,5-difluoroaniline 4-(3-Pyridyl)-3,5-difluoroaniline (PREPARATION 2, 625 mg, 3.03 mmol), sodium bicarbonate (382 mg, 4.55 mmol, 1.5 eq) and dry THF (60 ml) are combined. The resulting mixture is placed under an atmosphere of nitrogen and benzylchloro-formate (394 µl, 4.55 mmol, 1.5 eq) is added. The reaction is allowed to stir at 20°–25°. After this time, the reaction is added to methylene chloride (150 ml) and washed with saturated sodium bicarbonate then brine, dried (sodium sulfate), filtered and concentrated under reduced pressure to a solid which is puffed by silica gel chromatography (200 g of silica gel, eluted with acetonitrile/chloroform (3/97 - 11, 5/95 - 21), the title compound is recovered as a solid, mp 188°–190°; FTIR (neat) cm$^{-1}$ 3030, 1737, 1642, 1478, 1408, 1231, 1029, 723; MS (EI, m/z) 340, 296, 232, 205, 91, 79; NMR (CD$_3$CL$_3$) δ8.59, 8.53–8.51, 7.95–7.92, 7.56–7.51, 7.44–7.31, 7.28 and 5.21.

PREPARATION 4 N-Allyl-N-carbobenzyloxy-4-(3-pyridyl)-3,5-difluoroaniline

A mixture of N-carbobenzyloxy-4-(3-pyridyl)-3,5-difluoroaniline (PREPARATION 3, 543 mg, 1.60 mmol) in anhydrous THF (40 ml) is treated with sodium hydride (60% dispersion in mineral oil, 128 mg, 3.19 mmol, 2 eq). The reaction is kept under an atmosphere of nitrogen at 20°–25° for 0.5 hr. After this time, ally bromide (691 μl, 7.99 mmol, 5 eq) is added. Stirring is continued at 20°–25° for 16 hr. After this time, the reaction is carefully quenched with water (20 ml). The layers are separated and the aqueous layer is extracted with ethyl acetate (3×25 ml). The combined organics phases are washed with brine, dried (sodium sulfate), filtered and concentrated under reduced pressure. The concentrate is purified by silica gel chromatography (125 g of silica gel) eluting with acetonitrile/chloroform (3/97 - 11). The appropriate fractions are concentrated to give the title compound. An analytical sample is prepared by preparative TLC (SG, acetonitrile/chloroform -6/94), mp=92°–93°; FTIR (mull) cm$^{-1}$ 3068, 3061, 1710, 1705, 1643, 1635, 1412, 1263, 1024, 733; MS (EI) m/z: 380, 336, 309, 245, 91, 65; NMR (CDCl$_3$) 8.72, 8.62, 7.99, 7.42-7.36, 7.03, 5.94, 5.23–5.18 and 4.34 δ.

PREPARATION 5 (±)-5-(Iodomethyl)-3-[4-(3-pyridyl)-3,5-difluorophenyl]-2-oxazolidinone N-Allyl-N-carbobenzyloxy-4-(3-pyridyl)-3,5-difluoroaniline (PREPARATION 4, 496 mg 1.31 mmol) in chloroform (25 ml), pyridine (1.58 ml, 19.6 mmol, 15 eq) and iodine (4.97 g, 19.6 mmol, 15 eq) are combined. The resulting mixture is placed under an atmosphere of nitrogen and heated to 50° with stirring. After 1.5 hr, the reaction is decanted into chloroform (70 ml). The remaining sludge is rinsed with chloroform (3×15 ml). The combined organics are washed with sodium thiosulfate (20%), then brine, dried (sodium sulfate), filtered and concentrated under reduced pressure to give a solid. This material is purified by silica gel chromatography (100 g) eluting with methanol/chloroform (0.5/99.5–11, 1/99, 11). The appropriate fractions are pooled and concentrated to give the title compound, mp 133°–134°; FTIR (mull) cm$^{-1}$ 3130, 1758, 1650, 1414, 1241, 1017 and 846; NMR (CDCl$_3$) 8.72, 8.62, 7.79, 7.43–7.38, 7.32, 4.84–4.72, 4.19, 3.80, 3.51 and 3.39 δ.

PREPARATION 6 (±)-5-(Azidomethyl)-3-[4-(3-pyridyl)-3,5-difluorophenyl]-2-oxazolidinone (±)-5-(Iodomethyl)-3-[4-(3-pyridyl)-3,5-difluorophenyl]-2-oxazolidinone (PREPARATION 5, 577 mg, 1.31 mmol) in DMF (dried over 4A sieves, 15 ml) is combined with sodium azide (681 mg, 10.5 mmol, 8 eq). The reaction is placed under an atmosphere of nitrogen and heated to 55°. After 2 hr, the reaction is added to water (100 ml) and then extracted with ethyl acetate (4×25 ml). The combined organic extracts are combined and are washed with water then brine, dried (sodium sulfate), filtered and concentrated under reduced pressure. The crude azide is suitable for reduction without further purification. An analytical sample is prepared by preparative TLC (silica gel) eluting with acetonitrile/chloroform (10/90). The appropriate fractions are pooled and concentrated to give the title compound, mp 97°–98°; FTIR (mull) cm$^{-1}$ 3483, 2110, 1746, 1640, 1417, 1237, 1064 and 716; MS (EI, m/z) 331, 274, 258, 232, 217, 190 and 43; NMR (CDCl$_3$) 8.72, 8.63, 7.79, 7.42–7.38, 7.34, 4.90–4.82, 4.11, 3.88, 3.77 and 3.63 δ.

PREPARATION 7 (±)-5-(Aminomethyl)-3-[4-(3-pyridyl)-3,5-difluorophenyl]-2-oxazolidinone (±)-5-(Azidomethyl)-3-[4-(3-pyridyl)-3,5-difluorophenyl]-2-oxazolidinone (PREPARATION 6, 354 mg, ~1.07 mmol) in methanol (40 ml) and palladium on carbon (10%, 50 mg) are mixed. The mixture is purged with nitrogen and then placed under an atmosphere of hydrogen (1 atm). The reaction is allowed to stir at 20°–25° for 16 hrs. After this time, the reaction is filtered and concentrated under reduced pressure to a solid amine. The crude amine is suitable for acetylation without further purification. An analytical sample is prepared by preparative TLC (SG) methanol/chloroform (10/90). The title compound is recovered as a solid, mp 143°–145°; FTIR (neat) cm$^{-1}$ 3368, 1757, 1646, 1412, 1244, 1025 and 714; MS (EI, m/z) 305, 276, 233, 219, 44 and 29; NMR (CDCl$_3$) 8.71, 8.62, 7.79, 7.39, 7.33, 4.79–4.70, 4.06, 3.92, 3.18, 2.98 and 1.52 δ.

PREPARATION 8 4-(4-pyridyl)-3,5-difluoroaniline

Following the general procedure of PREPARATION 2 and making non-critical variations N,N-[1,2-bis(dimethylsilyl)ethane]-3,5-difluoroaniline (PREPARATION 1, 2.00 g 7.38 mmol) is transmetallated and combined with tetrakis(triphenylphosphine)palladium (0) (0.1 eq) and 4-bromopyridine (1 eq). The 4-bromopyridine is freshly prepared from the hydrochloric acid salt as described below. The salt is neutralized in excess saturated sodium bicarbonate. The free base is then extracted with diethyl ether. The combined organic extracts are dried over magnesium sulfate for 15 min, filtered, then concentrated under reduced pressure. The free base is stored in a stoppered flask, under nitrogen and frozen in dry ice prior to use. The free base quickly decomposes at 20°–25°. The reaction is worked up as previously described. The crude product is isolated. The NMR showed this material to be a mixture of desired product and its zinc chloride complex (~1:1). An analytical sample is prepared by preparative TLC (SG) eluting with acetonitrile/chloroform (10/90). NMR (CDCl$_3$) δ8.63, 7.38, 6.30 and 4.06.

PREPARATION 9 N-Carbobenzyloxy-4-(4-pyridyl)-3,5-difluoroaniline

Following the general procedure of PREPARATION 3 and making non-critical variations 4-(4-pyridyl)-3,5-difluoroaniline (PREPARATION 8, 236 mg, 1.15 mmol) is converted to the carbamate derivative. The crude product is purified by silica gel chromatography (100 g of SG, eluted with a 3–5% acetonitrile/chloroform gradient), the title compound is recovered as a solid, mp 185°–186°; FTIR (neat) cm$^{31\ 1}$ 1743, 1642, 1605, 1254, 1072; HRMS calc'd for C$_{19}$H$_{14}$F$_2$N$_2$O$_2$=340.1023, found=340.1029; MS (EI, m/z) 340, 232, 108, 91, 79, 43; NMR (CDCl$_3$) δ8.67, 7.43–7.38, 7.15, 5.23.

PREPARATION 10 N-Allyl-N-carbobenzyloxy-4-(4-pyridyl)-3,5-difluoroaniline

Following the general procedure of PREPARATION 4 and making non-critical variations but starting with N-carbobenzyloxy-4-(4-pyridyl)-3,5-difluoroaniline (PREPARATION 9, 468 mg, 1.38 mmol) is alkylated. The crude product is purified by silica gel (125 g) chromatography eluted with acetonitrile/chloroform (3/97, 21). The appropriate fractions are pooled and concentrated to give the title compound, mp 82°–83°; FTIR (neat) cm$^{-1}$ 1713, 1635, 1598, 1396, 1312, 1235, 1028; MS (EI, m/z) 380 [M$^+$], 330, 246, 219, 91, 40; NMR (CDCl$_3$) 8.69, 7.41–7.33, 7.03, 5.92, 5.25–5.17 and 4.34 δ.

PREPARATION 11 (±)-5-Iodomethyl-3-[4-(4-pyridyl)-3,5-difluorophenyl]-2-oxazolidinone Following the general procedure of PREPARATION 5 and making non-critical variations but starting with N-allyl-N-carbobenzyloxy-4-(4-pyridyl)-3,5-difluoroaniline (PREPARATION 10, 241 mg, 0.634 mmol) is converted to the oxazolidinone iodide. The crude product is not purified further. NMR (CDCl$_3$) δ8.70, 7.44, 7.32, 4.85–4.73, 4.19, 3.80, 3.50, 3.40.

PREPARATION 12 (R)-[3-(3-fluorophenyl)-2-oxo-5-oxazolidinyl]methyl butyrate

A mixture of lithium bromide (0.181 g, 2.08 mmol), tri-n-butylphosphine oxide (0.454 g, 2.08 nmol), and dry o-xylene (10 ml) is azeotropically dried for 1 hr. After cooling below the reflux point, a mixture of (R)-glycidyl butyrate (5.000 g, 34.68 mmol) and 3-fluorophenyl isocyanate (4.755 g or 3.96 ml, 34.68 mmol) in dry o-xylene (10 ml) is added over 10 min to the hot mixture (some refluxing observed during the addition). When the addition is complete, the mixture is heated to reflux for 2 hr and then allowed to cool to 20°–25°. The solvent is removed under reduced pressure and the residue chromatographed over silica gel, eluting with hexane/ethyl acetate (6:1, 4:1, and then 2:1), to give the title compound, [α]$^{25}_D$–46.7° (c 1.0, CHCl$_3$); IR (mineral oil mull) 1758, 1615, 1591, 1498, 1229, 1197, 1169 cm$^{-1}$; NMR (CDCl$_3$, 300 MHz) δ7.44, 7.34, 7.23, 6.86, 4.88, 4.39, 4.32, 4.13, 3.82, 2.33, 1.63, 0.92; MS (m/z) 281, 193, 180, 150, 148, 137, 123, 95, 43; HRMS (m/z) 281.1068 (calc'd for C$_{14}$H$_{16}$FNO$_4$=281.1063).

PREPARATION 13 (R)-3-(3-fluorophenyl)-5-(hydroxymethyl)-2-oxazolidinone

A mixture of (R)-[3-(3-fluorophenyl)-2-oxo-5-oxazolidinyl]methyl butyrate (PREPARATION 12, 2.789 g, 9.91 mmol) in methanol (10 ml) is treated with a 25 wt. % mixture of sodium methoxide in methanol (57 μl, 0.99 mmol) at 20°–25°. After 45 min as measured by TLC (methanol/chloroform, 5/95) the starting material has been consumed. The reaction mixture is carefully quenched by the addition of hydrochloric acid (1N, 0.99 ml, 0.99 mmol) and then concentrated under reduced pressure. Chromatography of the concentrate over silica gel, eluting first with hexane/ethyl acetate (1/1), and then ethyl acetate, pooling and concentrating the appropriate fractions gives the title compound, mp 106.5°–107.5°; [α]$^{25}_D$–66.8° (c 1.1, CH$_3$CN); IR (mineral oil mull): 3520, 1724, 1612, 1590, 1496, 1428, 1420, 1232 and 1199 cm$^{-1}$; NMR (CDCl$_3$, 300 MHz) δ7.44, 7.32, 7.23, 6.84, 4.77, 4.07–3.96, 3.76 and 2.44; MS (m/z) 211, 180, 136, 124, 95; HRMS (m/z) 211.0641 (calc'd for C$_{10}$H$_{10}$FNO$_3$: 211.0645).

The enantiomeric excess of the oxazolidinone alcohol is determined by reacting it with (R)-(+)-α-methoxy-α-(trifluoromethyl)phenylacetic acid (DCC, DMAP, methylene chloride at 20°–25°), and examining the NMR spectrum of the resultant Mosher ester. The enantiomeric excess is estimated to be ≧95%.

PREPARATION 14 (R)-3-(3-fluorophenyl)-5-(hydroxymethyl)-2-oxooxazolidine

A mixture of N-(carbobenzyloxy)-3-fluoroaniline (1.000 g, 4.08 mmol) in dry tetrahydrofuran (10 ml) is cooled with a dry ice/acetone bath to about −78° and then n-butyllithium (1.87 ml of a 1.6M minute in hexanes, 2.91 mmol) is added.

(R)-glycidyl butyrate (0.420 g or 0.413 ml, 2.91 mmol) is then added via syringe and the cooling bath allowed to dissipate overnight, with the reaction mixture reaching 20°–25°. The reaction mixture is quenched by the careful addition of saturated aqueous ammonium chloride, the entire mixture transferred to a separatory funnel with dichloromethane washings, and the mixture extracted with dichloromethane. The combined organic extracts are dried over sodium sulfate, filtered and concentrated under reduced pressure to give a concentrate which is purified by chromatography over silica gel, eluting with acetonitrile/chloroform (10/90) containing 1% methanol, to give the title compound.

PREPARATION 15 (R)-[3-(3-fluorophenyl)-2-oxo-5-oxazolidinyl]methyl 4-methylbenzenesulfonate A mixture of (R)-3-(3-fluorophenyl)-5-(hydroxymethyl)-2-oxooxazolidine (PREPARATION 14, 1.800 g, 8.52 mmol) in dry pyridine (10 ml) is cooled to 5° and then treated with p-toluenesulfonyl chloride (1.706 g, 8.95 mmol). The mixture is left at this temperature overnight. TLC with methanol/chloroform (5/95) or hexane/ethyl acetate (1/1) indicates the starting material is consumed. The reaction mixture is dropped into ice water (30 ml) and the resultant precipitate collected by vacuum filtration through a medium-porosity sintered glass funnel. The collected solids are thoroughly washed with cold water, dried under reduced pressure and recrystallized from ethyl acetate hexane to give the title compound, mp 114°–115°; [α]$^{25}_D$–62.6° (c 1.0, CH$_3$CN); IR (mineral oil mull): 1751, 1617, 1591, 1499, 1415, 1362, 1227, 1202, 1191, 1172, 1093, 967 cm$^{-1}$; NMR (CDCl$_3$, 300 MHz) δ7.78, 7.38, 7.36, 7.33, 7.16, 6.86, 4.84, 4.29, 4.24, 4.10, 3.88, 2.46; MS (m/z) 365, 149, 122, 91; HRMS (m/z) 365.0738 (calc'd for C$_{17}$H$_{16}$FNO$_5$S: 365.0733).

PREPARATION 16 (R)-[3-(3-fluorophenyl)-2-oxo-5-oxazolidinyl]methyl azide

A mixture of (R)-[3-(3-fluorophenyl)-2-oxo-5-oxazolidinyl]methyl 4-methylbenzenesulfonate (PREPARATION 15, 2.340 g, 6.40 mmol) in dry DMF (60 ml) is treated with solid sodium azide (3.331 g, 51.23 mmmol) at 20°–25°. The resultant slurry is warmed to 65° for 4.5 hr and then cooled to 20°–25° and left overnight. The reaction mixture is then diluted with ethyl acetate and water, transferred to a separatory funnel, and extracted with ethyl acetate. The combined ethyl acetate extracts are washed thoroughly with water, and then dried (sodium sulfate), filtered and concentrated under reduced pressure to give the title compound, mp 81°–82°; [α]$^{25}_D$–136.5° (c 0.9, CHCl$_3$); IR (mineral oil mull): 2115, 1736, 1614, 1591, 1586, 1497, 1422, 1233, 1199, 1081, 1049 cm$^{-1}$; NMR (CDCl$_3$, 300 MHz) δ7.45, 7.34, 7.23, 6.86, 4.81, 4.09, 3.86, 3.72 and 3.60; MS (m/z) 236 (59.0, M$^+$), 179, 136, 122, 109, 95, 75; HRMS (m/z) 236.0708 (calc'd for C$_{10}$H$_9$FN$_4$O$_2$: 236.0709).

PREPARATION 17 (S)-N-[[3-(3-fluorophenyl)-2-oxo-5-oxazolidinyl]methyl]acetamide

A mixture of (R)-[3-(3-fluorophenyl)-2-oxo-5-oxazolidinyl]methyl azide (PREPARATION 16, 8.200 g, 34.71 mol) in ethyl acetate (100 ml) is treated with palladium on carbon (10%, 0.820 g) under nitrogen. The atmosphere is then replaced with hydrogen (balloon) via repeated evacuation and filling. After stirring under hydrogen for 17 hr, TLC in methanol/chloroform (5/95) reveals the azide starting material is consumed. The atmosphere is replaced with nitrogen and then pyridine (6 ml) and acetic anhydride (4.1 ml, 43.40 mmol) are added to the reaction mixture. The reaction mixture is stirred for 1 hr at 20°–25° and then filtered through Celite, washing the pad with ethyl acetate.

The filtrate is concentrated under reduced pressure and the residue taken-up in dichloromethane. The addition of ether affords a precipitate. After standing in the refrigerator overnight the solids are collected by vacuum filtration, washed with cold hexane, and dried under reduced pressure to give the title compound as a solid. The crude product is purified by chromatography over silica gel, eluting with methanol/chloroform (5/95). The appropriate fractions are pooled and concentrated to give the title compound, mp 140.0°–140.5°; $[\alpha]^{25}_D$ –6.6° (c 1.0, CHCl$_3$).

PREPARATION 18 (S)-N-[[3-(3-fluoro-4-iodophenyl)-2-oxo-5-oxazolidinyl]methyl]acetamide (S)-N-[[3-(3-fluorophenyl)-2-oxo-5-oxazolidinyl]methyl]- acetamide (PREPARATION 17, 0.280 g, 1.11 mmol) is dissolved in a mixture of acetic acid (20 ml) and trifluoroacetic acid (5 ml) and then treated with iodine monochloride (2.343 g, 14.43 mmol) at 20°–25°. The mixture is stirred at 20°–25° under nitrogen. After about 24 hr the reaction mixture is diluted with ether and the solids collected under reduced pressure through a medium-porosity sintered glass filter, washing with ether. The crude solids are dissolved in hot chloroform (a little methanol is added), transferred to a separatory funnel, and washed with saturated aqueous sodium bicarbonate, 20% aqueous sodium thiosulfate and brine. The organic phase is separated, dried over sodium sulfate, filtered and concentrated under reduced pressure to give the title compound, mp 185.5°–186.5°; $[\alpha]^{25}_D$–37.6° (c 1.0, DMF). PREPARATION 19 (±)-N-[[3-[3-fluoro-4-(trimethylstannyl)phenyl]-2-oxo-5-oxazolidinyl]-methyl]acetamide In 1,4-dioxane (10 ml) is combined (3S)-N-[[3-(3-fluoro-4-iodophenyl)-2-oxo-5-oxazolidinyl]methyl]acetamide (PREPARATION 18, 0.091 g, 0.24 mmol), bis(triphenylphosphine)-palladium (II) chloride (0.017 g, 0.024 mmol) and hexamethylditin (0.105 g, 0.321 mmol). The reaction mixture is thoroughly purged with nitrogen and heated to reflux temperature for 1.5 hr. After this time, the reaction is concentrated under reduced pressure and then purified by silica gel chromatography (10 g of silica gel; eluted with 100 ml each of 0.5, 1, and finally 1.5% methanol/chloroform). After concentration of appropriate fractions, the racemic title compound is obtained, mp: 127°–130°; NMR (CDCl$_3$, 300 MHz) 7.38–7.33, 7.19, 6.04, 4.83–4.72, 4.05, 3.76, 3.71–3.59, 2.02 and 0.34 δ; MS (m/z) 415 (3, M+), 401, 165, 139, 56, 43.

EXAMPLE 1

(±)-5-(Acetamidomethyl)3-[4-(3-pyridyl)-3,5-difluorophenyl]-2-oxazolidinone (±)-5-(Aminomethyl)-3-[4-(3-pyridyl)-3,5-difluorophenyl]-2-oxazolidinone (PREPARATION 7, 135 mg, 0.433 mmol) in anhydrous methylene chloride (10 ml), pyridine (143 µl, 1.77 mmol, 4 eq) and acetic anhydride (167 µl, 1.77 mmol, 4 eq) are combined. The reaction is allowed to stir at 20°–25° under nitrogen. After 2.5 hr the reaction is added to methylene chloride (30 ml) and washed with saturated sodium bicarbonate then brine, dried (sodium sulfate), filtered and concentrated under reduced pressure to a solid. This material is purified by silica gel (70 g) chromatography eluted with methanol/chloroform (1/99–4/96 gradient). The appropriate fractions are pooled and concentrated to give the title compound, mp 218°–219°; PTIR (mull) cm$^{-1}$ 3347, 1742, 1679, 1648, 1568, 1409, 1247, 1022, 755; MS (EI, m/z) 347 [M$^+$], 303, 275, 244, 219, 73, 56; NMR (CDCl$_3$) 8.68, 8.59, 7.85, 7.48–7.41, 7.31, 4.87–4.79, 4.10, 3.82, 3.72–3.57, 2.03 δ.

EXAMPLE 1a (±)-5-(Acetamidomethy)-3-[4-(3-pyridyl)-3,5-difluorophenyl]-2-oxazolidinone methanesulfonic acid salt (±)-5-(Acetamidomethyl)3-[4-(3-pyridyl)]-3,5-difluorophenyl-2-oxazolidinone (EXAMPLE 1, 74 mg, 0.21 mmol) and methanesulfonic acid (14 µl, 0.21 mmol) are combined in methanol (4 ml). The mixture is warmed to reflux temperature for 3 min and the reaction becomes homogeneous. The reaction is cooled to 20°–25° and concentrated under reduced pressure to a solid. The solid is triturated with ether and the recovered solid is dissolved in water (8 ml), filtered and lyophilized, to give the title compound, mp 203°–205°.

EXAMPLE 2

(±)-5-(acetamidomethyl)3-[4-(4-pyridyl)]-3,5-difluorophenyl-2-oxazolidinone (±)-5-Iodomethyl-3-[4-(4-pyridyl)-3,5-difluorophenyl]-2-oxazolidinone (PREPARATION 11, 213 mg) and sodium azide (166 mg, 2.56 mmol, –5 eq) are combined in DMF (10 ml, dried over 4A sieves). The reaction is placed under an atmosphere of nitrogen and heated to 55°. After 2 hr, the reaction is complete by TLC acetonitrile/methylene chloride (6/94). The reaction mixture is added to water (50 ml) and extracted with ethyl acetate (5×25 ml). The combined organic extracts are washed with water, then brine, dried over sodium sulfate, filtered and concentrated under reduced pressure to an oil (CAUTION: Azides are known to decompose explosively). The crude material is combined with methanol (20 ml) and palladium on carbon (10%, 30 mg). The reaction is purged with nitrogen then placed under an atmosphere of hydrogen. After 16 hr, the reaction is filtered and concentrated under reduced pressure to a solid. This material is combined with acetic anhydride (64 µl) and pyridine (55 µl) in methylene chloride (11 ml). The reaction is stirred at 20°–25° under nitrogen for 12 hr. After this time, the reaction is added to 50 ml of methylene chloride and washed with saturated sodium bicarbonate then brine, dried (sodium sulfate), filtered and concentrated under reduced pressure to an oil. The final product is purified by silica gel chromatography (100 g of silica gel, eluting with a methanol/chloroform 1–4% gradient). ccc, mp 147°–149°; FTIR (neat) cm$^{-1}$1741, 1651, 1646, 1412, 1246, 1027, 745; MS (EI, m/z) 347, 303, 243, 219, 206, 58, 29; NMR (CDCl$_3$) δ8.70, 7.42, 7.29, 6.10, 4.90–4.78, 4.08, 3.82, 3.73–3.67, 2.05.

EXAMPLES 3–54

Following the general procedure of Preparations 1–11 and the above EXAMPLES, and (i) starting with the aniline REAGENT (I) listed below for each example, and (ii) using the appropriate aryl or heteroaryl iodide, bromide, triflate or fluorosulfonate for the palladium-mediated coupling reaction (IV→V), the TITLE COMPOUND for the respective EXAMPLE is obtained.

| EXAMPLE | REAGENT | TITLE COMPOUND |
| --- | --- | --- |
| 3 | 3,5-difluoroaniline | (±)-5-(acetamidomethyl)-3-[4-(2,6-dimethylpyridin-4-yl)-3,5-difluorophenyl]-2-oxazolidinone |
| 4 | 3,5-difluoroaniline | ([±)-5-(acetamidomethyl)-3-[4-(2-methylpyridin-4-yl)-3,5-difluorophenyl]-2-oxazolidinone |
| 5 | 3,5-difluoroaniline | (±)-5-(acetamidomethyl)-3-[4-(2-ethylpyridin-4-yl)-3,5-difluorophenyl]-2-oxazolidinone |
| 6 | 3,5-difluoroaniline | (±)-5-(acetamidomethyl)-3-(4-phenyl-3,5-difluorophenyl)-2-oxazolidinone |
| 7 | 3,5-difluoroaniline | (±)-5-(acetamidomethyl)-3-[4-(4-(dimethylamino)phenyl)-3,5-difluorophenyl]-2-oxazolidinone |
| 8 | 3,5-dichloroaniline | (±)-5-(acetamidomethyl)-3-[4-(3-pyridyl)-3,5-dichlorophenyl]-2-oxazolidinone |
| 9 | 3,5-dichloroaniline | (±)-5-(acetamidomethyl)-3-[4-(4-pyridyl)-3,5-dichlorophenyl]-2-oxazolidinone |
| 10 | 3,5-dichloroaniline | (±)-5-(acetamidomethyl)-3-(4-phenyl-3,5-dichlorophenyl)-2-oxazolidinone |
| 11 | 3-fluoroaniline | (±)-5-(acetamidomethyl)-3-[4-(3-pyridyl)-3-fluorophenyl]-2-oxazolidinone |
| 12 | 3-fluoroaniline | (±)-5-(acetamidomethyl)-3-[4-(4-pyridyl)-3-fluorophenyl]-2-oxazolidinone |
| 13 | 3-fluoroaniline | (±)-5-(acetamidomethyl)-3-[4-(2,6-dimethylpyridin-4-yl)-3-fluorophenyl]-2-oxazolidinone |
| 14 | 3-fluoroaniline | (±)-5-(acetamidomethyl)-3-[4-(2-methylpyridin-4-yl)-3-fluorophenyl]-2-oxazolidinone |
| 15 | 3-fluoroaniline | (±)-5-(acetamidomethyl)-3-[4-(2-ethylpyridin-4-yl)-3-fluorophenyl]-2-oxazolidinone |
| 16 | 3-fluoroaniline | (±)-5-(acetamidomethyl)-3-(4-phenyl-3-fluorophenyl)-2-oxazolidinone |
| 17 | 3-fluoroaniline | (±)-5-(acetamidomethyl)-3-[4-(4-(dimethylamino)phenyl)-3-fluorophenyl]-2-oxazolidinone |
| 18 | 3-chloroaniline | (±)-5-(acetamidomethyl)-3-[4-(3-pyridyl)-3-chlorophenyl]-2-oxazolidinone |
| 19 | 3-chloroaniline | (±)-5-(acetamidomethyl)-3-[4-(4-pyridyl)-3-chlorophenyl]-2-oxazolidinone |
| 20 | 3-chloroaniline | (±)-5-(acetamidomethyl)-3-(4-phenyl-3-chlorophenyl)-2-oxazolidinone |
| 21 | 3,5-bis(trifluoromethyl)aniline | (±)-5-(acetamidomethyl)-3-[4-(3-pyridyl)-3,5-bis(trifluoromethyl)phenyl]-2-oxazolidinone |
| 22 | 3,5-bis(trifluoromethyl)aniline | (±)-5-(acetamidomethyl)-3-[4-(4-pyridyl)-3,5-bis(trifluoromethyl)phenyl]-2-oxazolidinone |
| 23 | 3,5-bis(trifluoromethyl)aniline | (±)-5-(acetamidomethyl)-3-[4-phenyl-3,5-bis(trifluoromethyl)phenyl]-2-oxazolidinone |
| 24 | 3-(trifluoromethyl)-aniline | (±)-5-(acetamidomethyl)-3-[4-(3-pyridyl)-3-(trifluoromethyl)phenyl]-2-oxazolidinone |
| 25 | 3-(trifluoromethyl)-aniline | (±)-5-(acetamidomethyl)-3-[4-(4-pyridyl)-3-(trifluoromethyl)phenyl]-2-oxazolidinone |
| 26 | 3-(trifluoromethyl)-aniline | (±)-5-(acetamidomethyl)-3-[4-phenyl-3-(trifluoromethyl)phenyl]-2-oxazolidinone |
| 27 | 3,5-dimethoxy-aniline | (±)-5-(acetamidomethyl)-3-[4-(3-pyridyl)-3,5-dimethoxyphenyl]-2-oxazolidinone |
| 28 | 3,5-dimethoxy-aniline | (±)-5-(acetamidomethyl)-3-[4-(4-pyridyl)-3,5-dimethoxyphenyl]-2-oxazolidinone |
| 29 | 3,5-dimethoxy-aniline | (±)-5-(acetamidomethyl)-3-(4-phenyl-3,5-dimethoxyphenyl)-2-oxazolidinone |
| 30 | m-anisidine | (±)-5-(acetamidomethyl)-3-[4-(3-pyridyl)-3-methoxyphenyl]-2-oxazolidinone |
| 31 | m-anisidine | (±)-5-(acetamidomethyl)-3-[4-(4-pyridyl)-3-methoxyphenyl]-2-oxazolidinone |
| 32 | m-anisidine | (±)-5-(acetamidomethyl)-3-(4-phenyl-3-methoxyphenyl)-2-oxazolidinone |
| 33 | 3,5-difluoroaniline | (±)-5-(acetamidomethyl)-3-[4-(5-indolyl)-3,5-difluorophenyl]-2-oxazolidinone |
| 34 | 3,5-difluoroaniline | (±)-5-(acetamidomethyl)-3-[4-(3-quinolyl)-3,5-difluorophenyl]-2-oxazolidinone |
| 35 | 3,5-difluoroaniline | (±)-5-(acetamidomethyl)-3-[4-(4-quinolyl)-3,5-difluorophenyl]-2-oxazolidinone |
| 36 | 3,5-difluoroaniline | (±)-5-(acetamidomethyl)-3-[4-(6-quinolyl)-3,5-difluorophenyl]-2-oxazolidinone |
| 37 | 3,5-difluoroaniline | (±)-5-(acetamidomethyl)-3-[4-(4-isoquinolyl)-3,5-difluorophenyl]-2-oxazolidinone |
| 38 | 3,5-difluoroaniline | (±)-5-(acetamidomethyl)-3-[4-(1-methyl-5-indolyl)-3,5-difluorophenyl]-2-oxazolidinone |
| 39 | 3,5-difluoroaniline | (±)-5-(acetamidomethyl)-3-[4-(6-benzothiazolyl)-3,5-difluorophenyl]-2-oxazolidinone |
| 40 | 3,5-difluoroaniline | (±)-5-(acetamidomethyl)-3-[4-(6-benzoxazolyl)-3,5-difluorophenyl]-2-oxazolidinone |

-continued

| EXAMPLE | REAGENT | TITLE COMPOUND |
|---|---|---|
| 41 | 3,5-difluoroaniline | (±)-5-(acetamidomethyl)-3-[4-(2-dimethylamino)-4-thiazolyl)-3,5-difluorophenyl]-2-oxazolidinone |
| 42 | 3,5-difluoroaniline | (±)-5-(acetamidomethyl)-3-[4-(2-amino-4-thiazolyl)-3,5-difluorophenyl]-2-oxazolidinone |
| 43 | 3,5-difluoroaniline | (±)-5-(acetamidomethyl)-3-[4-(2-(dimethylamino)-4-oxazolyl)-3,5-difluorophenyl]-2-oxazolidinone |
| 44 | 3,5-difluoroaniline | (±)-5-(acetamidomethyl)-3-[4-(2-amino-4-oxazolyl)-3,5-difluorophenyl]-2-oxazolidinone |
| 45 | 3-fluoroaniline | (±)-5-(acetamidomethyl)-3-[4-(3-quinolyl)-3-fluorophenyl]-2-oxazolidinone |
| 46 | 3-fluoroaniline | (±)-5-(acetamidomethyl)-3-[4-(4-quinolyl)-3-fluorophenyl]-2-oxazolidinone |
| 47 | 3-fluoroaniline | (±)-5-(acetamidomethyl)-3-[4-(6-quinolyl)-3-fluorophenyl]-2-oxazolidinone |
| 48 | 3-fluoroaniline | (±)-5-(acetamidomethyl)-3-[4-(4-isoquinolyl)-3-fluorophenyl]-2-oxazolidinone |
| 49 | 3-fluoroaniline | (±)-5-(acetamidomethyl)-3-[4-(5-indolyl)-3-fluorophenyl]-2-oxazolidinone |
| 50 | 3-fluoroaniline | (±)-5-(acetamidomethyl)-3-[4-(1-methyl-5-indolyl)-3-fluorophenyl]-2-oxazolidinone |
| 51 | 3-fluoroaniline | (±)-5-(acetamidomethyl)-3-[4-(6-benzothiazolyl)-3-fluorophenyl]-2-oxazolidinone |
| 52 | 3-fluoroaniline | (±)-5-(acetamidomethyl)-3-[4-(6-benzoxazolyl)-3-fluorophenyl]-2-oxazolidinone |
| 53 | 3-fluoroaniline | (±)-5-(acetamidomethyl)-3-[4-(2-amino-4-thiazolyl)-3-fluorophenyl]-2-oxazolidinone |
| 54 | 3-fluoroaniline | (±)-5-(acetamidomethyl)-3-[4-(2-amino-4-oxazolyl)-3-fluorophenyl]-2-oxazolidinone |

EXAMPLE 55

(±)-N-[[3-[3-fluoro-4-(6-quinolyl)phenyl]-2-oxo-5-oxazolidinyl]methyl]acetamide (±)-N-[[3-[3-fluoro-4-(trimethylstannyl)phenyl]-2-oxo-5-oxazolidinyl]methyl]acetamide (PREPARATION 19, 0.367 g, 0.88 mmol), 6-bromoquinoline (0.239 g, 1.15 mmol) and bis(triphenyl-phosphine)palladium(II) chloride (0.062 g, 0.088 mmol) are combined with DMF (10 ml). The reaction mixture is thoroughly purged with nitrogen and then heated to 80° under nitrogen. After 2 hr, little progress is noted by TLC and so the reaction mixture is heated to 95° for a further 2 hr. At this point, TLC revealed the reaction is complete. The mixture is cooled to 20°–25° and concentrated under reduced pressure to give a crude material which is purified by chromatography over silica gel (10 g of silica gel; eluted with methanol/chloroform, 1→4%) to give the racemic title compound, mp 216°–219° (dec); IR (internal reflectance) 3411, 3281, 1743, 1657, 1630, 1566, 1521, 1499, 1416, 1226, 1194 cm$^{-1}$; NMR (CDCl$_3$, 300 MHz) 8.95, 8.26–8.20, 8.00, 7.92, 7.61, 7.57, 7.47, 7.35, 6.08, 4.84, 4.13, 3.86, 3.80–3.62, 2.05 δ; MS (m/z) 379 (100.0, M$^+$), 335, 307, 276, 264, 251.

EXAMPLE 56

(S)-N-[[3-[3-fluoro-4-(4-pyridyl)phenyl]-2-oxo-5-oxazolidinyl]methyl]acetamide

A slurry of (±)-N-[[3-(3-fluoro-4-iodophenyl)-2-oxo-5-oxazolidinyl]methyl]acetamide (PREPARATION 18, 0.063 g, 0.165 mmol) and trimethyl(4-pyridyl)tin (0.060 g, 0.248 mmol) in 1,4-dioxane (5 ml) is degassed by repeated evacuation and filing with nitrogen. Bis(triphenylphosphine)palladium (II) chloride (0.012 g, 0.0165 mmol) is added, the reaction again degassed, and then the mixture is brought to reflux under nitrogen. After 4 hr TLC (silica gel, 10% methanol/chloroform) reveals some of the iodide still remains. The mixture is refluxed a further 20 hr, cooled to 20°–25°, and concentrated under reduced pressure. The residue is chromatographed over silica gel, eluting with a little chloroform and then methanol/chloroform (1%, 2%, and then 5%). The appropriate fractions are pooled and concentrated to give the enantiomerically enriched title compound, mp 190.5°–191.0°; [α]25$_D$ −16.4° (c 0.5, CHCl$_3$). The following characteristics are noted for a racemic sample, mp 179°–180°; IR (internal reflectance) 3279, 3063, 1756, 1752, 1657, 1626, 1600, 1542, 1522, 1485, 1412, 1407, 1377, 1222, 1198 cm$^{-1}$; NMR (CDCl$_3$, 300 MHz) 8.67, 7.59, 7.50, 7.47, 7.33, 6.15, 4.84, 4.11, 3.85, 3.78–3.62, 2.04 δ; MS (m/z) 329 (39.8, M$^+$), 285, 257, 201, 172, 73 and 42.

CHART A

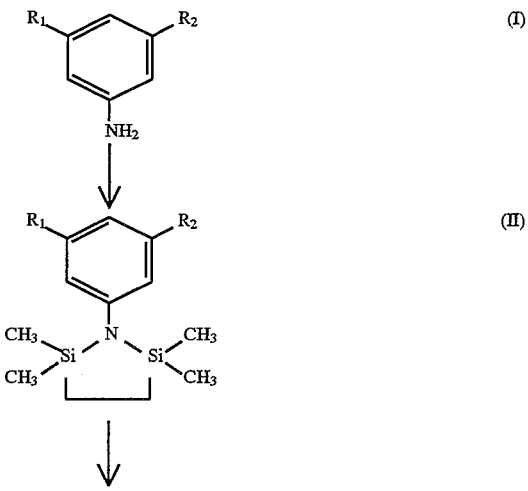

CHART A
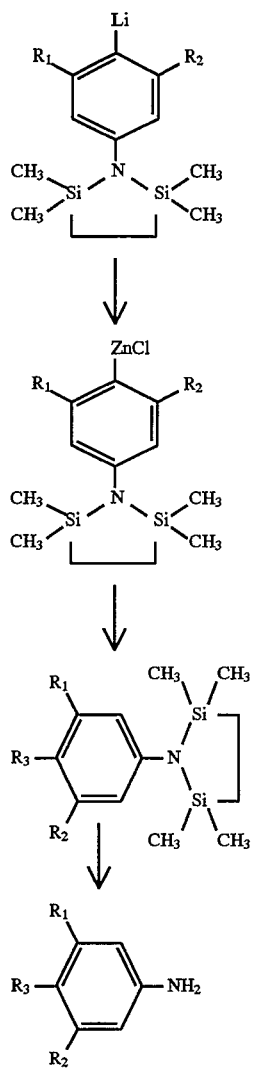
CHART B
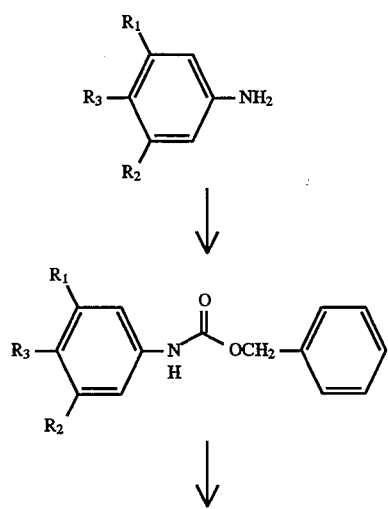
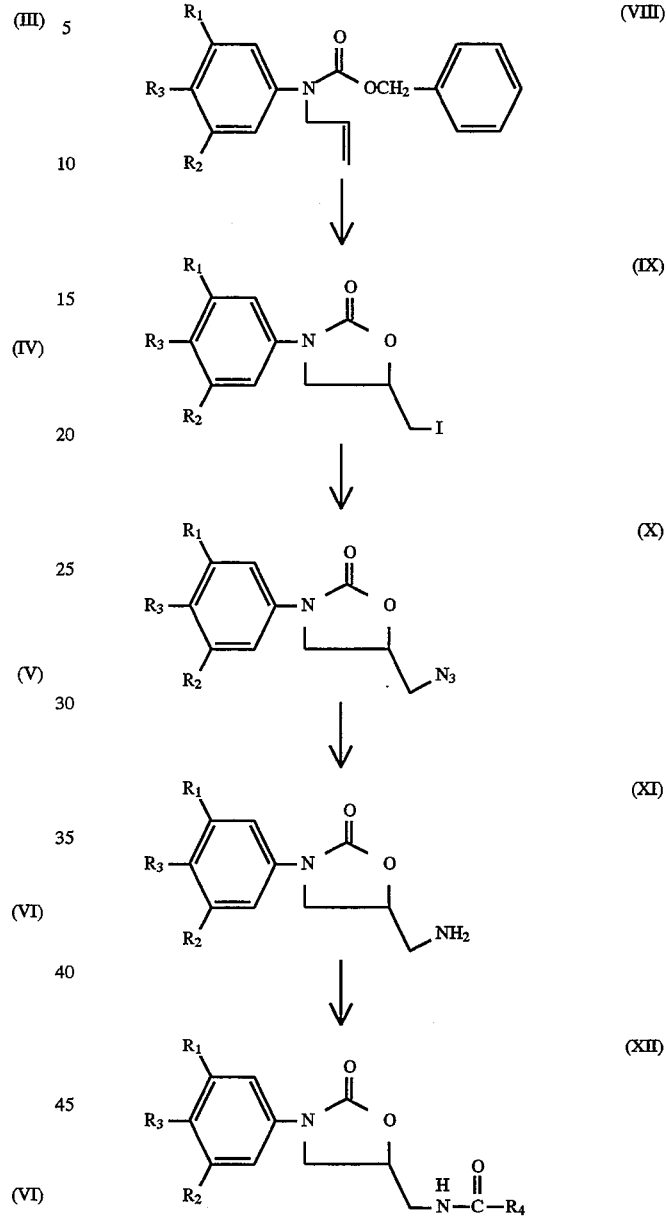
CHART C
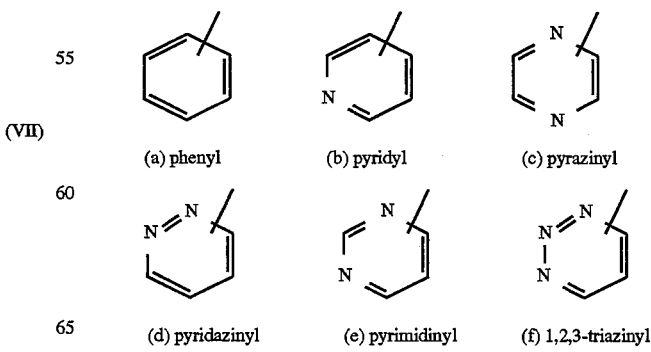
(a) phenyl  (b) pyridyl  (c) pyrazinyl
(d) pyridazinyl  (e) pyrimidinyl  (f) 1,2,3-triazinyl -continued
CHART C

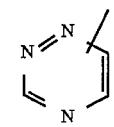
(g) 1,2,4-triazinyl

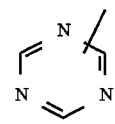
(h) 1,2,5-triazinyl

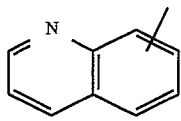
(i) quinolinyl

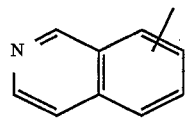
(j) isoquinolinyl

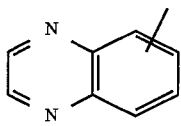
(k) quinoxalinyl

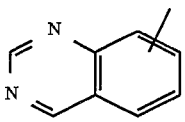
(l) quinazolinyl

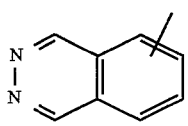
(m) phthalazinyl

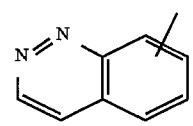
(n) cinnolinyl

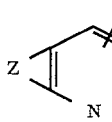
(o) napthyridinyl

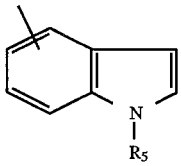
(p) indolyl

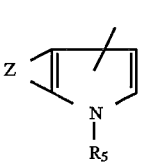
(q) pyrrolopyridinyl

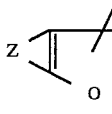
(r) furanopyridinyl

(s) thienopyridinyl

-continued
CHART C

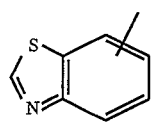
(t) benzothiazolyl

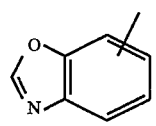
(v) benzoxazolyl

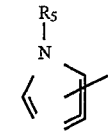
(v) imidazolyl

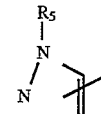
(w) pyrazolyl

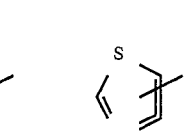
(x) thiazolyl

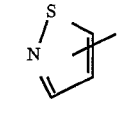
(y) isothiazolyl

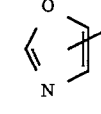
(z) oxazolyl

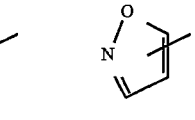
(aa) isoxazolyl

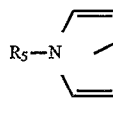
(bb) pyrrolyl

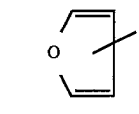
(cc) furanyl

(dd) thiophenyl

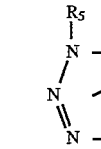
(ee) 1,2,3-triazolyl

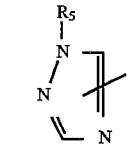
(ff) 1,2,4-triazolyl

CHART D
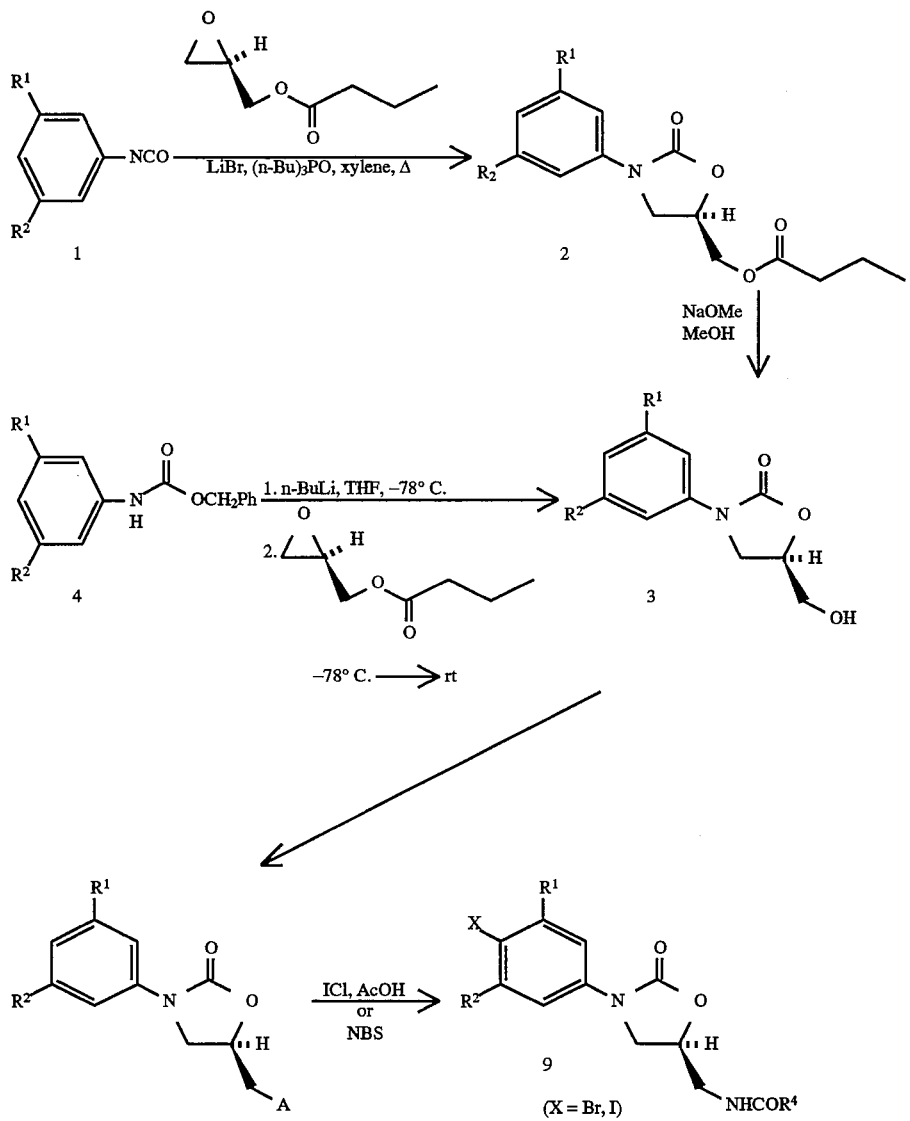
5: A = OTs or OMs
6: A = N₃
7: A = NH₂
8: A = NHCOR⁴

CHART E

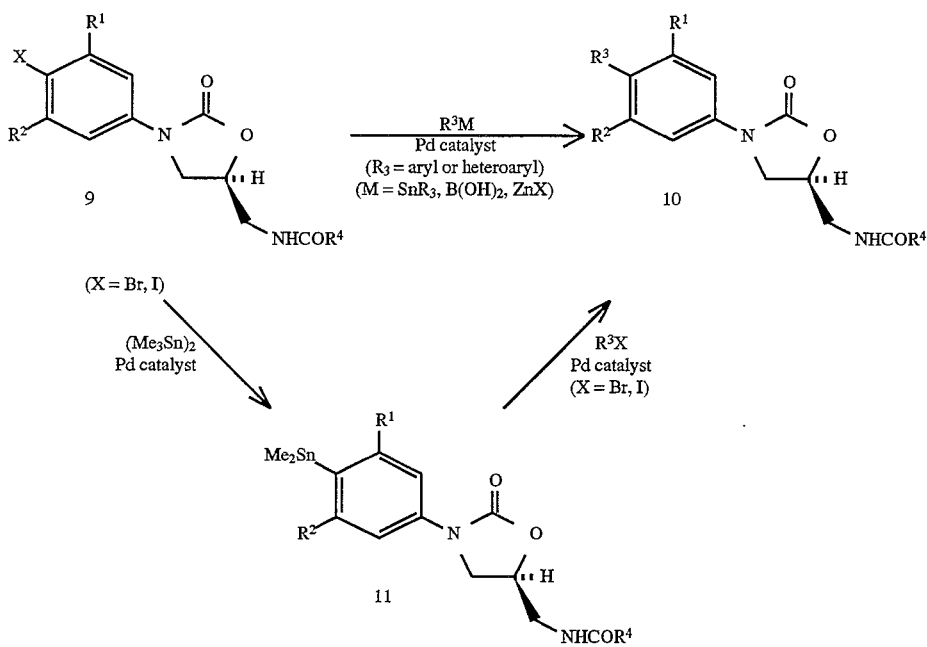

We claim:

1. A substituted hetemarylphenyl oxazolidinone of formula (XII)

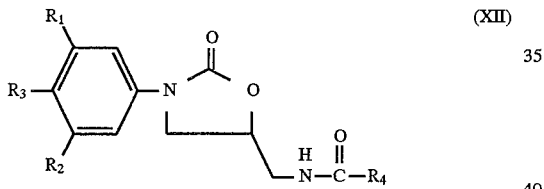

where (I) $R_1$ and $R_2$ are the same or different and are selected from the group consisting of
(a) —H,
(b) —F,
(c) —Cl
(d) —$CF_3$, and
(e) —$OCH_3$, provided that only one of $R_1$ or $R_2$ may be hydrogen;

(II) $R_3$ is selected from the group consisting of
(c) pyrazinyl, (d) pyridazinyl (e) pyrimidinyl, (k) q-inoxalinyl, (l) quiazolinyl, (m) phthalazinyl, (n) cinnolinyl, (o) naphthyridinyl, (q) pyrrolopyridinyl having the saturated nitrogen substituted with $R_{5-1}$ where $R_{5-1}$ is
—H,
$C_1$–$C_4$ alkyl optionally substituted with one or more halogens,
$C_{3-6}$ cycloalkyl, or
—C(O)$R_{5-2}$ where $R_{5-2}$ is:
—H,
$C_1$–$C_4$ alkyl optionally substituted with one or more halogens, or
phenyl optionally substituted with one or more halogens,
(v) imidazolyl having the saturated nitrogen substituted with $R_{5-1}$ where $R_{5-1}$ is as defined above, (w) pyrazolyl having the saturated nitrogen substituted with $R_{5-1}$ where $R_{5-1}$ is as defined above,
where substituents (c), (d), (e), (k), (l), (m), (n), (o), (q), (v) and (w) are optionally substituted with X and Y;

(III) each occurrence of Y is independently selected from
(a) —H,
(b) –F, (c) —Cl, (d) —Br, (e) —I,
(f) —$R_{3-1}$, (g) —$OR_{3-1}$ where $R_{3-1}$ is H or $Cl_1$–$C_4$ alkyl, or
(h) —$NO_2$;

(IV) each occurrence of X is independently selected from
(a) —H,
(b) $C_1$–$C_8$ alkyl optionally substituted with one or more halogens,
—OH,
=O other than at alpha position,
—S(O)n$R_{3-2}$ where $R_{3-2}$ is $C_1$–$C_4$ alkyl or $C_3$–$C_8$ cycloalkyl, or
—$NR_{3-3}R_{3-4}$ where $R_{3-3}$ and $R_{3-4}$ are the same or different and are —H, $C_1$–$C_8$ alkyl, $C_3$–$C_8$ cycloalkyl, —$(CH_2)_r$CHOR$_{3-5}$, —$(CH_2)_r$NR$_{3-6}$R$_{3-7}$, or taken together are —$(CH_2)O(CH_2)$—, —$(CH_2)_r$CH(CO)R$_{3-8}$, or —$(CH_2)N (R_{3-8})(CH_2)_2$— where $R_{3-5}$ is —H or $C_1$–$C_4$ alkyl, or
$R_{3-6}$ and $R_{3-7}$ are the same or different and are —H, $C_1$–$C_4$ alkyl or taken together are —$(CH_2)_r$—,
(c) $C_2$–$C_5$ alkenyl,
(d) $C_3$–$C_8$ cycloalkyl,
(e) —$OR_{3-3}$ where $R_{3-3}$ is as defined above,
(f) —CN,
(g) —S—(O)$_n$—$R_{3-8}$ where $R_{3-8}$ is $C_1$–$C_4$ alkyl optionally substituted with one or more halogens,
—OH,
—CN,
—$NR_{3-3}R_{3-4}$ where $R_{3-3}$ and $R_{3-4}$ are as defined above,
—$CO_2R_{3-5}$ where $R_{3-5}$ is as defined above, $C_2$–$C_4$ alkenyl, $NR_{3-9}R_{3-10}$ where $R_{3-9}$ is —H, $C_1$–$C_4$ alkyl, or $C_3$–$C_8$ cycloalkyl and $R_{3-10}$ is —H, $C_1$–$C_4$ alkyl, $C_1$–$C_4$ alkenyl, $C_3$–$C_4$ cycloalkyl, —$OR_{3-5}$, or —$NR_{3-6}R_{3-7}$ where $R_{3-5}$, $R_{3-6}$, and $R_{3-7}$ are as defined above, —$N_3$, —NHC(O)$R_{3-11}$ where $R_{3-11}$ is $C_1$–$C_4$ alkyl optionally substituted with one or more halogens, (h) —S(O)$_2$—N=S(O)$_p R_{3-14}R_{3-15}$ where $R_{3-4}$ and $R_{3-5}$ are the same or different and are $C_{1-C2}$ alkyl, or taken together are —(CH$_2$)$_q$—, (i) —S—C(O)—$R_{3-11}$ where $R_{3-11}$ is as defined above, (j) tetrazoly, (k) —$NR_{3-3}R_{3-4}$ where $R_{3-3}$ and $R_{3-4}$ are as defined above, (l) —$N(R_{3-3})COR_{3-11}$ where $R_{3-3}$ and $R_{3-11}$ are as defined above, (m) —$N(R_{3-3})S(O)_n R_{3-11}$ where $R_{3-3}$ and $R_{3-11}$ are as defined above, (n) —$CONR_{3-3}R_{3-4}$ where $R_{3-3}$ and $R_{3-4}$ are as defined above, (o) —$C(O)R_{3-16}$ where $R_{3-16}$ is

—H, $C_1C_8$ alkyl optionally substituted with one or more halogens, $C_1$–$C_4$ alkyl optionally substituted with

—$OR_{3-5}$,

—$OC(O)R_{3-5}$,

—$NR_{3-3}R_{3-4}$,

—$S(O)_n R_{3-17}$, $C_3$–$C_8$ cycloalkyl, or $C_2$–$C_5$ alkenyl optionally substituted with —CHO or —$CO_2 R_{3-5}$, where $R_{3-3}$, $R_{3-4}$, and $R_{3-5}$ are as defined above and $R_{3-17}$ is $C_1$–$C_4$ alkyl or $C_3$–$C_8$ cycloalkyl, (p) —C(=$NR_{3-18}$)$R_{3-16}$ where $R_{3-16}$ is as defined above and $R_{3-18}$ is —$NR_{3-3}R_{3-4}$, —$OR_{3-3}$, or —NHC(O)$R_{3-3}$ where $R_{3-3}$ and $R_{3-4}$ are as defined above, (q) —$CR_{3-16}(OR_{3-19})OR_{3-20}$ where $R_{3-16}$ is as defined above and $R_{3-19}$ and $R_{3-20}$ are the same or different and are $C_1$–$C_4$ alkyl, or taken together are —(CH$_2$)$_m$—,

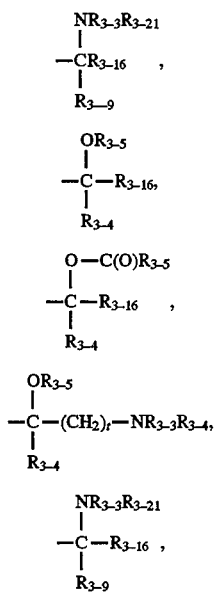

where $R_{3-3}$, $R_{3-4}$, $R_{3-5}$, $R_{3-9}$, and $R_{3-16}$ are as defined above and $R_{3-21}$ is $R_{3-4}$ or —$NR_{3-4}R_{3-5}$ where $R_{3-4}$ and $R_{3-5}$ are as defined above, m is 2 or 3;

n is 0, 1, or 2;

p is 0 or 1;

q is 3, 4 or 5;

t is 1, 2 or 3;

(v) $R_4$ is selected from the group consisting of
(a) —H,
(b) $C_1$–$C_{12}$ alkyl optionally substituted with 1–3 Cl,
(c) $C_3$–$C_{12}$ cycloalkyl,
(d) $C_5$–$C_{12}$ alkenyl containing one double bond,
(e) phenyl optionally substituted with 1–3 —OH, —OCH$_3$, —OC$_2$H$_5$, —NO$_2$, —F, —Cl, —Br, —COOH and SO$_3$H, —N(R$_{4-1}$)(R$_{4-2}$) where $R_{4-1}$ and $R_{4-2}$ are the same or different and are —H and $C_1$–$C_5$ alkyl,
(f) furanyl,
(g) tetrahydrofuranyl,
(h) 2-thiophene,
(i) pyrrolidinyl,
(j) pyridinyl,
(k) —O—$R_{4-3}$ where $R_{4-3}$ is $C_1$–$C_4$ alkyl,
(l) —NH$_2$,
(m) —NHR$_{4-4}$ where $R_{4-4}$ is $C_1$–$C_3$ alkyl or $\phi$,
(n) —NR$_{4-4}R_{4-5}$ where $R_{4-4}$ is as defined above and $R_{4-5}$ is $C_1$–$C_3$ alkyl, or taken together with the attached nitrogen atom to form a saturated mononitrogen $C_5$–$C_7$ heterocyclic ring optionally containing —O—
(o) —CH$_2$—OH,
(p) CH$_2$—OR$_{4-6}$ where $R_{4-6}$ is $C_1$–$C_4$ alkyl or —CO—$R_{4-7}$ where $R_{4-7}$ is $C_{1-4}$ alkyl or —$\phi$;and pharmaceutically acceptable salts thereof.

2. A compound according to claim 1 where one of $R_1$ or $R_2$ are hydrogen.

3. A compound according to claim 1 where $R_3$ is (c) pyrazinyl.

4. A compound according to claim 1 where $R_3$ is (d) pyridazinyl.

5. A compound according to claim 1 where $R_3$ is (e) pyrimidinyl.

6. A compound according to claim 1 where $R_3$ is (k) quinoxalinyl.

7. A compound according to claim 1 where $R_3$ is (l) quinazolinyl.

8. A compound according to claim 1 where $R_3$ is (m) phthalazinyl.

9. A compound according to claim 1 where $R_3$ is (n) cinnolinyl.

10. A compound according to claim 1 where $R_3$ is (o) naphthyridinyl.

11. A compound according to claim 1 where $R_3$ is (q) pyrrolopyridinyl having the saturated nitrogen substituted with $R_{5-1}$.

12. A compound according to claim 1 where $R_3$ is (v) imidazolyl having the saturated nitrogen substituted with $R_{5-1}$.

13. A compound according to claim 1 where $R_3$ is (w) pyrazolyl having the saturated nitrogen substituted with $R_{5-1}$.

14. A compound according to claim 1 where $R_1$ and $R_2$ are other than hydrogen.

15. A compound according to claim 14 where $R_3$ is (c) pyrazinyl.

16. A compound according to claim 14 where $R_3$ is (d) pyridazinyl.

17. A compound according to claim 14 where $R_3$ is (e) pyrimidinyl.

18. A compound according to claim 14 where $R_3$ is (k) quinoxalinyl.

19. A compound according to claim 14 where $R_3$ is (l) quinazolinyl.

20. A compound according to claim 14 where $R_3$ is (m) phthalazinyl.

21. A compound according to claim 14 where $R_3$ is (n) cinnolinyl.

22. A compound according to claim 14 where $R_3$ is (o) naphthyridinyl.

23. A compound according to claim 14 where $R_3$ is (q) pyrrolopyridinyl having the saturated nitrogen substituted with $R_{5-1}$.

24. A compound according to claim 14 where $R_3$ is (v) imidazolyl having the saturated nitrogen substituted with $R_{5-1}$.

25. A compound according to claim 14 where $R_3$ is (w) pyrazolyl having the saturated nitrogen substituted with $R_{5-1}$.

\* \* \* \* \*